(12) United States Patent
Cao et al.

(10) Patent No.: US 12,416,587 B2
(45) Date of Patent: Sep. 16, 2025

(54) IMAGING SYSTEM HAVING RADIATION DETECTORS OF DIFFERENT ORIENTATIONS

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 509 days.

(21) Appl. No.: 17/365,299

(22) Filed: Jul. 1, 2021

(65) Prior Publication Data
US 2021/0325319 A1    Oct. 21, 2021

Related U.S. Application Data

(63) Continuation of application No. PCT/CN2019/071122, filed on Jan. 10, 2019.

(51) Int. Cl.
*A61B 6/00*     (2024.01)
*G01N 23/046*   (2018.01)
*G01T 1/29*     (2006.01)

(52) U.S. Cl.
CPC ......... *G01N 23/046* (2013.01); *G01T 1/2928* (2013.01); *G01N 2223/401* (2013.01)

(58) Field of Classification Search
CPC .......... G01N 23/046; G01N 2223/401; G01N 2223/501; G01N 23/04; G01T 1/2928;
(Continued)

(56) References Cited

U.S. PATENT DOCUMENTS

2006/0039537 A1   2/2006  Strobel
2011/0064193 A1   3/2011  Minnigh et al.
(Continued)

FOREIGN PATENT DOCUMENTS

CN        1658793 A       8/2005
CN      101500488 A       8/2009
(Continued)

*Primary Examiner* — David P Porta
*Assistant Examiner* — Mamadou Faye
(74) *Attorney, Agent, or Firm* — IPro, PLLC

(57) ABSTRACT

Disclosed herein is system comprising: a radiation source; an image sensor; wherein the image sensor comprises a first radiation detector and a second radiation detector, respectively comprising a planar surface configured to receive radiation from the radiation source; wherein the planar surface of the first radiation detector and the planar surface of the second radiation detector are not parallel; wherein the first radiation detector and the second radiation detector are configured to move to a plurality of positions relative to the radiation source; wherein the image sensor is configured to capture, by using the first radiation detector and the second radiation detector and with the radiation, images of portions of a scene at the positions respectively, and configured to form an image of the scene by stitching the images of the portions; wherein the system is configured to rotate relative to the scene about a third axis.

21 Claims, 25 Drawing Sheets

(58) Field of Classification Search
CPC ...... G01T 1/16; G01T 1/24; A61B 6/4241; A61B 6/4452; A61B 6/5241; A61B 6/4266; A61B 6/03; A61B 6/4233; G01V 5/0066
See application file for complete search history.

(56) References Cited

U.S. PATENT DOCUMENTS

| | | |
|---|---|---|
| 2011/0096894 A1 | 4/2011 | Uehara et al. |
| 2015/0078525 A1 | 3/2015 | Hofmann et al. |
| 2015/0119704 A1* | 4/2015 | Roth ............... A61B 6/4258 600/425 |
| 2017/0020475 A1* | 1/2017 | Spahn ............... A61B 6/5205 |

FOREIGN PATENT DOCUMENTS

| | | |
|---|---|---|
| CN | 101862197 A | 10/2010 |
| CN | 103226114 A | 7/2013 |
| CN | 108836376 A | 11/2018 |
| CN | 108474651 B | 9/2020 |
| DE | 102008019646 A1 | 10/2009 |
| EP | 2633293 B1 | 5/2019 |
| EP | 2915488 B1 | 6/2019 |
| EP | 3847485 A4 | 4/2022 |
| JP | 2006192164 A | 7/2006 |
| WO | 2016147844 A1 | 9/2016 |
| WO | 2018002655 A1 | 1/2018 |

* cited by examiner

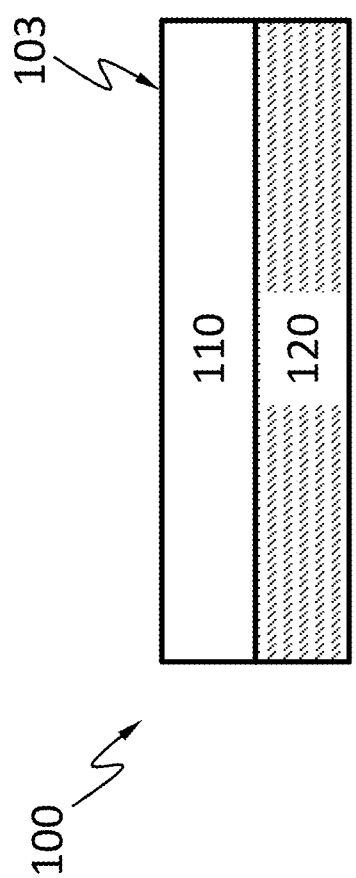

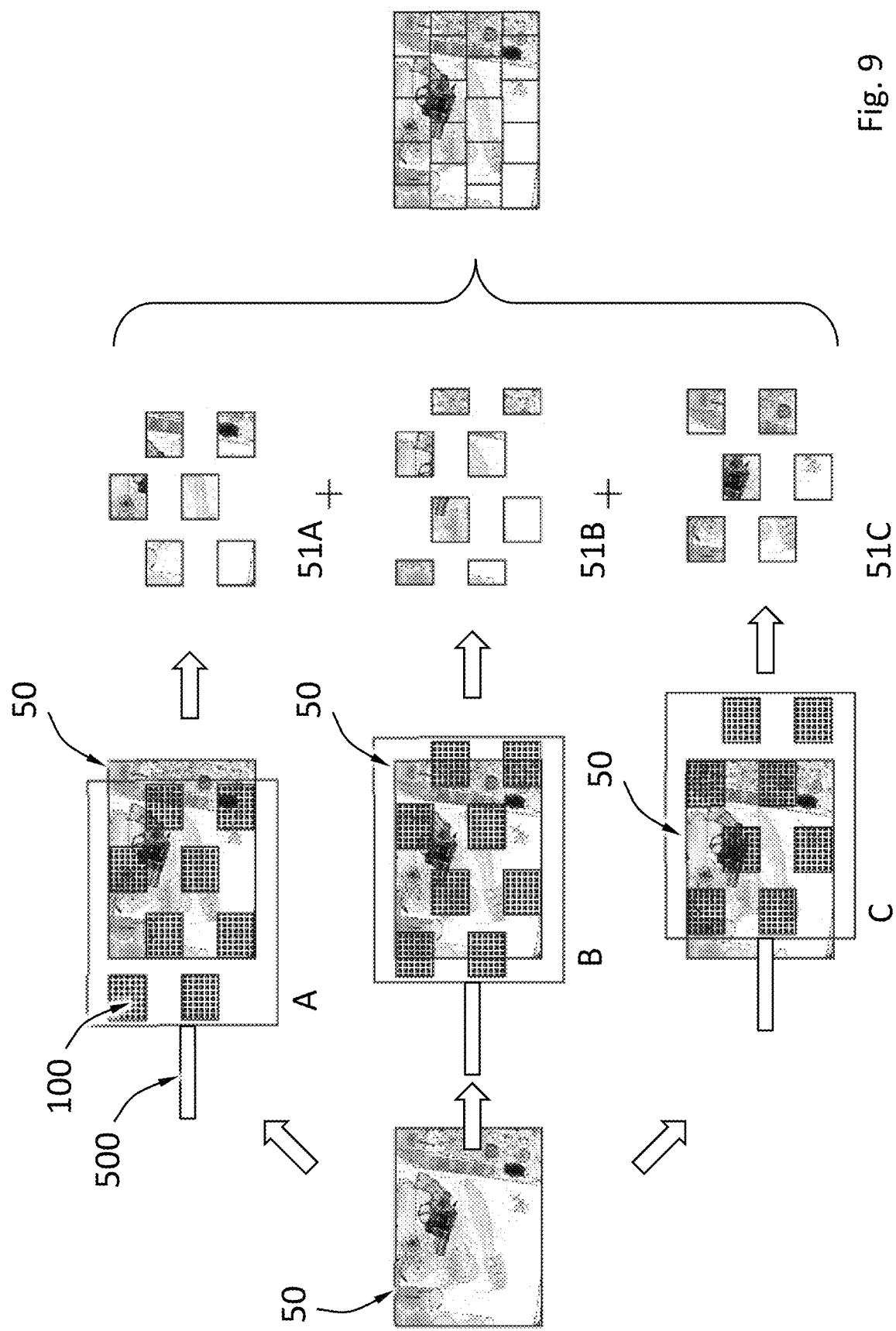

IMAGING SYSTEM HAVING RADIATION DETECTORS OF DIFFERENT ORIENTATIONS

BACKGROUND

Radiation detectors may be devices used to measure the flux, spatial distribution, spectrum or other properties of radiations.

Radiation detectors may be used for many applications. One important application is imaging. Radiation imaging is a radiography technique and can be used to reveal the internal structure of a non-uniformly composed and opaque object such as the human body.

Early radiation detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of radiation detectors are radiation image intensifiers. Components of a radiation image intensifier are usually sealed in a vacuum. In contrast to photographic plates, photographic films, and PSP plates, radiation image intensifiers may produce real-time images, i.e., do not require post-exposure processing to produce images. Radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus has to strike a compromise between absorption efficiency and resolution.

Semiconductor radiation detectors largely overcome this problem by direct conversion of radiation into electric signals. A semiconductor radiation detector may include a semiconductor layer that absorbs radiation in wavelengths of interest. When a radiation particle is absorbed in the semiconductor layer, multiple charge carriers (e.g., electrons and holes) are generated and swept under an electric field towards electric contacts on the semiconductor layer. Cumbersome heat management required in currently available semiconductor radiation detectors (e.g., Medipix) can make a detector with a large area and a large number of pixels difficult or impossible to produce.

SUMMARY

Disclosed herein is system comprising: a radiation source; an image sensor; wherein the image sensor comprises a first radiation detector and a second radiation detector, respectively comprising a planar surface configured to receive radiation from the radiation source; wherein the planar surface of the first radiation detector and the planar surface of the second radiation detector are not parallel; wherein the first radiation detector and the second radiation detector are configured to move to a plurality of positions relative to the radiation source; wherein the image sensor is configured to capture, by using the first radiation detector and the second radiation detector and with the radiation, images of portions of a scene at the positions respectively, and configured to form an image of the scene by stitching the images of the portions; wherein the system is configured to rotate relative to the scene about a third axis.

According to an embodiment, a relative position of the first radiation detector with respect to the second radiation detector remains the same.

According to an embodiment, the first radiation detector and the second radiation detector are configured to move relative to the radiation source by rotating about a first axis relative to the radiation source.

According to an embodiment, the first axis is parallel to the planar surface of the first radiation detector and the planar surface of the second radiation detector.

According to an embodiment, the first radiation detector and the second radiation detector are configured to move relative to the radiation source by rotating about a second axis relative to the radiation source, wherein the second axis is different from the first axis.

According to an embodiment, the radiation source is on the first axis.

According to an embodiment, the first radiation detector and the second radiation detector are configured to move relative to the radiation source by translating along a first direction relative to the radiation source.

According to an embodiment, the first direction is parallel to the planar surface of the first radiation detector and the planar surface of the second radiation detector.

According to an embodiment, the first direction is parallel to the planar surface of the first radiation detector but not parallel to the planar surface of the second radiation detector.

According to an embodiment, the first radiation detector and the second radiation detector are configured to move relative to the radiation source by translating along a second direction relative to the radiation source; wherein the second direction is different from the first direction.

According to an embodiment, the first radiation detector and the second radiation detector each comprise an array of pixels.

According to an embodiment, the first radiation detector is rectangular in shape.

According to an embodiment, the first radiation detector is hexagonal in shape.

According to an embodiment, the radiation source is on the third axis.

According to an embodiment, the image sensor is on the third axis.

According to an embodiment, the system is configured to rotate relative to the scene about a fourth axis different from the third axis.

According to an embodiment, the radiation source is on the fourth axis.

According to an embodiment, the image sensor is on the fourth axis.

According to an embodiment, the image sensor is configured to form images of the scene when the system is respectively at a plurality of rotational positions relative to the scene.

Disclosed herein is a method using the system described above, wherein the method comprising: forming a first image of the scene with the image sensor while the system is at a first rotational position relative to the scene; rotating the system relative to the scene about the third axis to a second rotational position relative to the scene; forming a second image of the scene with the image sensor while the system is at the second rotational position relative to the scene.

According to an embodiment, the radiation source is on the third axis.

According to an embodiment, the image sensor is on the third axis.

According to an embodiment, the method further comprises rotating the system relative to the scene about a fourth axis to a third rotational position relative to the scene; and forming a third image of the scene with the image sensor while the system is at the third rotational position relative to the scene; wherein the fourth axis is different from the third axis.

According to an embodiment, the radiation source is on the fourth axis.

According to an embodiment, the image sensor is on the fourth axis.

BRIEF DESCRIPTION OF FIGURES

FIG. 2A schematically shows a cross-sectional view of a radiation detector, according to an embodiment.

FIG. 9 schematically shows the image sensor capturing images of portions of a scene, according to an embodiment.

DETAILED DESCRIPTION

Figure 1:
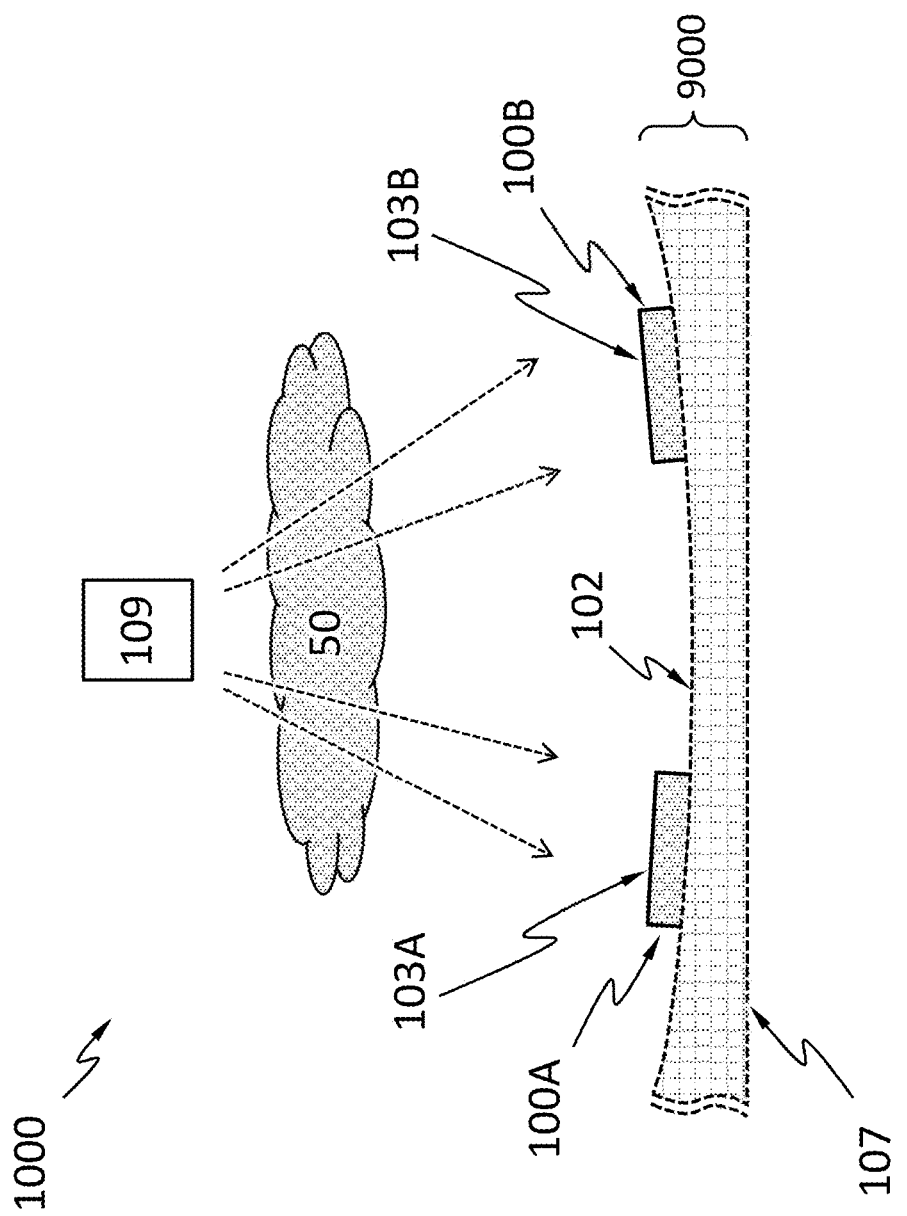
FIG. 1 schematically shows a cross-sectional view of a portion of an imaging system, according to an embodiment.

FIG. 1 schematically shows a cross-sectional view of an imaging system 1000 comprising a radiation source 109 and an image sensor 9000, according to an embodiment. The image sensor 9000 may have a plurality of radiation detectors 100 (e.g., a first radiation detector 100A, a second radiation detector 100B). The image sensor 9000 may have a support 107 with a curved surface 102. The plurality of radiation detectors may be arranged on the curved surface 102, as shown in the example of FIG. 1. The first radiation detector 100A may have a first planar surface 103A configured to receive radiation from the radiation source 109. The second radiation detector 100B may have a second planar surface 103B configured to receive the radiation from the radiation source 109. The first planar surface 103A and the second planar surface 103B may be not parallel. The radiation from the radiation source 109 may have passed through a scene 50 (e.g., a portion of a human body) before reaching the first radiation detector 100A or the second radiation detector 100B. The first radiation detector 100A and the second radiation detector 100B may be configured to move to a plurality of positions relative to the radiation source 109. The system 1000, including the radiation source 109 and the radiation detectors 100 (e.g., 100A and 100B) together, may be configured to rotate relative to the scene 50. The radiation source 109 may be an X-ray source or gamma ray source.

FIG. 2A schematically shows a cross-sectional view of one radiation detector 100, according to an embodiment. The radiation detector 100 may be used in the image sensor 9000. The radiation detector 100 may include a radiation absorption layer 110 and an electronics layer 120 (e.g., an ASIC) for processing or analyzing electrical signals incident radiation generates in the radiation absorption layer 110. In an embodiment, the radiation detector 100 does not comprise a scintillator. The radiation absorption layer 110 may include a semiconductor material such as, silicon, germanium, GaAs, CdTe, CdZnTe, or a combination thereof. The semiconductor may have a high mass attenuation coefficient for the radiation energy of interest. The surface 103 of the radiation absorption layer 110 distal from the electronics layer 120 is configured to receive radiation.

Figure 2B:
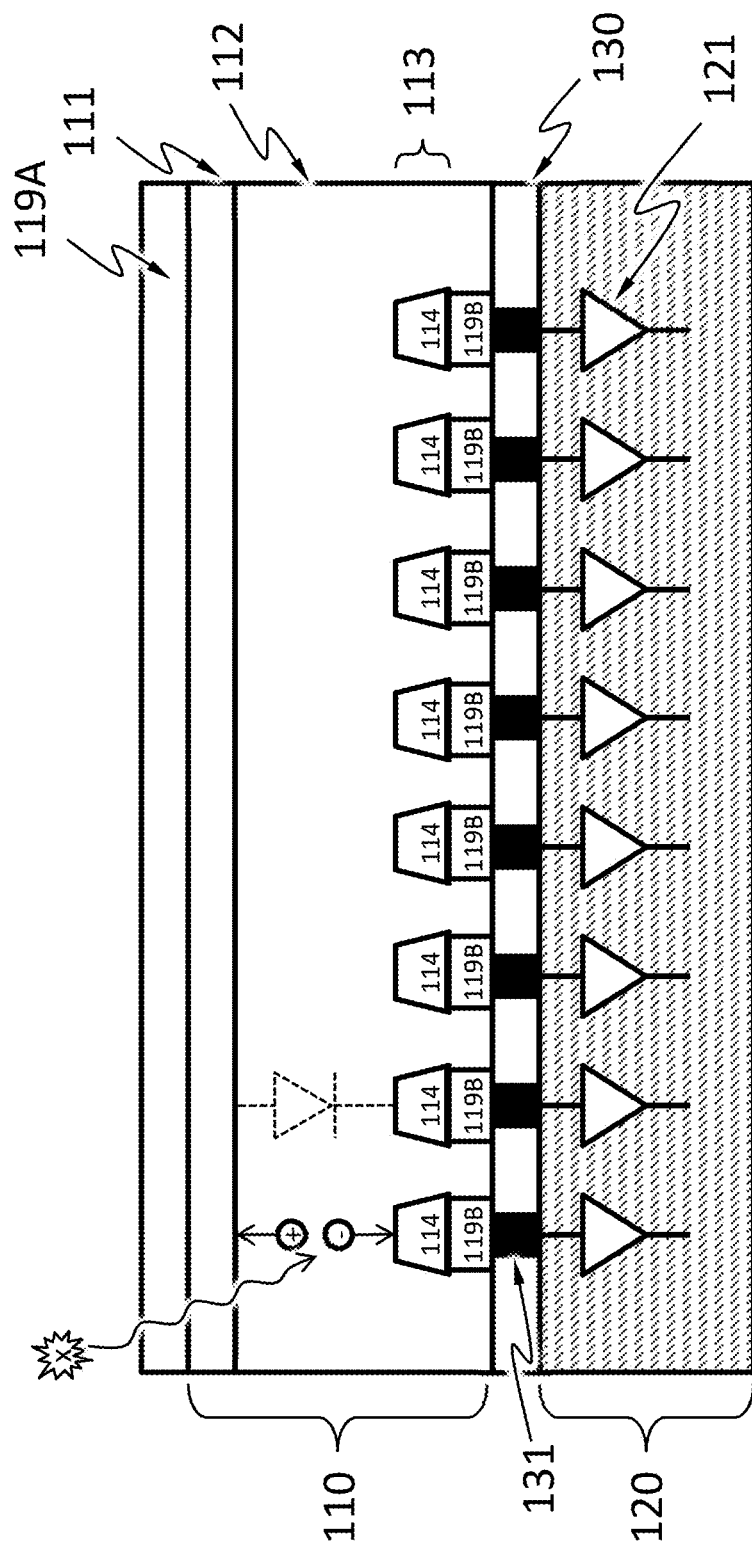
FIG. 2B schematically shows a detailed cross-sectional view of the detector, according to an embodiment.

As shown in a detailed cross-sectional view of the radiation detector 100 in FIG. 2B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 2B, each of the discrete regions 114 of the second doped region 113 forms a diode with the first doped region 111 and the optional intrinsic region 112. Namely, in the example in FIG. 2B, the radiation absorption layer 110 has a plurality of diodes having the first doped region 111 as a shared electrode. The first doped region 111 may also have discrete portions.

When a radiation particle hits the radiation absorption layer 110 including diodes, the radiation particle may be absorbed and generate one or more charge carriers by a number of mechanisms. A radiation particle may generate 10 to 100000 charge carriers. The charge carriers may drift to the electrodes of one of the diodes under an electric field. The field may be an external electric field. The electric contact 119B may include discrete portions each of which is in electrical contact with the discrete regions 114. In an embodiment, the charge carriers may drift in directions such that the charge carriers generated by a single radiation particle are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a radiation particle incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a radiation particle incident therein at an angle of incidence of 0° flow to the discrete region 114. Namely, less than 2%, less than 1%, less than 0.1%, or less than 0.01% of these charge carriers flow beyond the pixel.

Figure 2C:
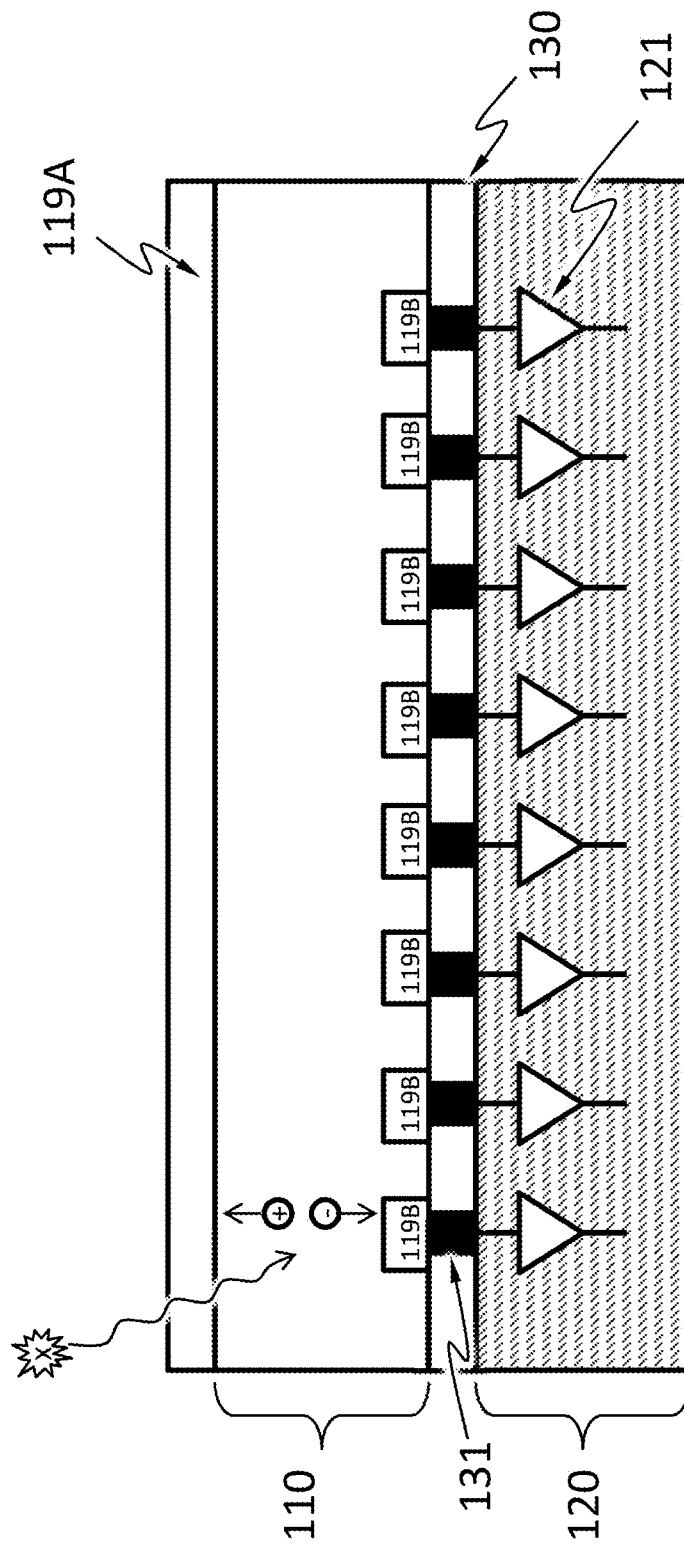
FIG. 2C schematically shows an alternative detailed cross-sectional view of the detector, according to an embodiment.

As shown in an alternative detailed cross-sectional view of the radiation detector 100 in FIG. 2C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation energy of interest.

When a radiation particle hits the radiation absorption layer 110 including a resistor but not diodes, it may be absorbed and generate one or more charge carriers by a number of mechanisms. A radiation particle may generate 10 to 100000 charge carriers. The charge carriers may drift to the electric contacts 119A and 119B under an electric field. The field may be an external electric field. The electric contact 119B includes discrete portions. In an embodiment, the charge carriers may drift in directions such that the charge carriers generated by a single radiation particle are not substantially shared by two different discrete portions of the electric contact 119B ("not substantially shared" here means less than 2%, less than 0.5%, less than 0.1%, or less than 0.01% of these charge carriers flow to a different one of the discrete portions than the rest of the charge carriers). Charge carriers generated by a radiation particle incident around the footprint of one of these discrete portions of the electric contact 119B are not substantially shared with another of these discrete portions of the electric contact 119B. A pixel 150 associated with a discrete portion of the electric contact 119B may be an area around the discrete portion in which substantially all (more than 98%, more than 99.5%, more than 99.9% or more than 99.99% of) charge carriers generated by a radiation particle incident at an angle of incidence of 0° therein flow to the discrete portion of the electric contact 119B. Namely, less than 2%, less than 0.5%, less than 0.1%, or less than 0.01% of these charge carriers flow beyond the pixel associated with the one discrete portion of the electric contact 119B.

The electronics layer 120 may include an electronic system 121 suitable for processing or interpreting signals generated by radiation particles incident on the radiation absorption layer 110. The electronic system 121 may include an analog circuitry such as a filter network, amplifiers, integrators, and comparators, or a digital circuitry such as a microprocessor, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 3:
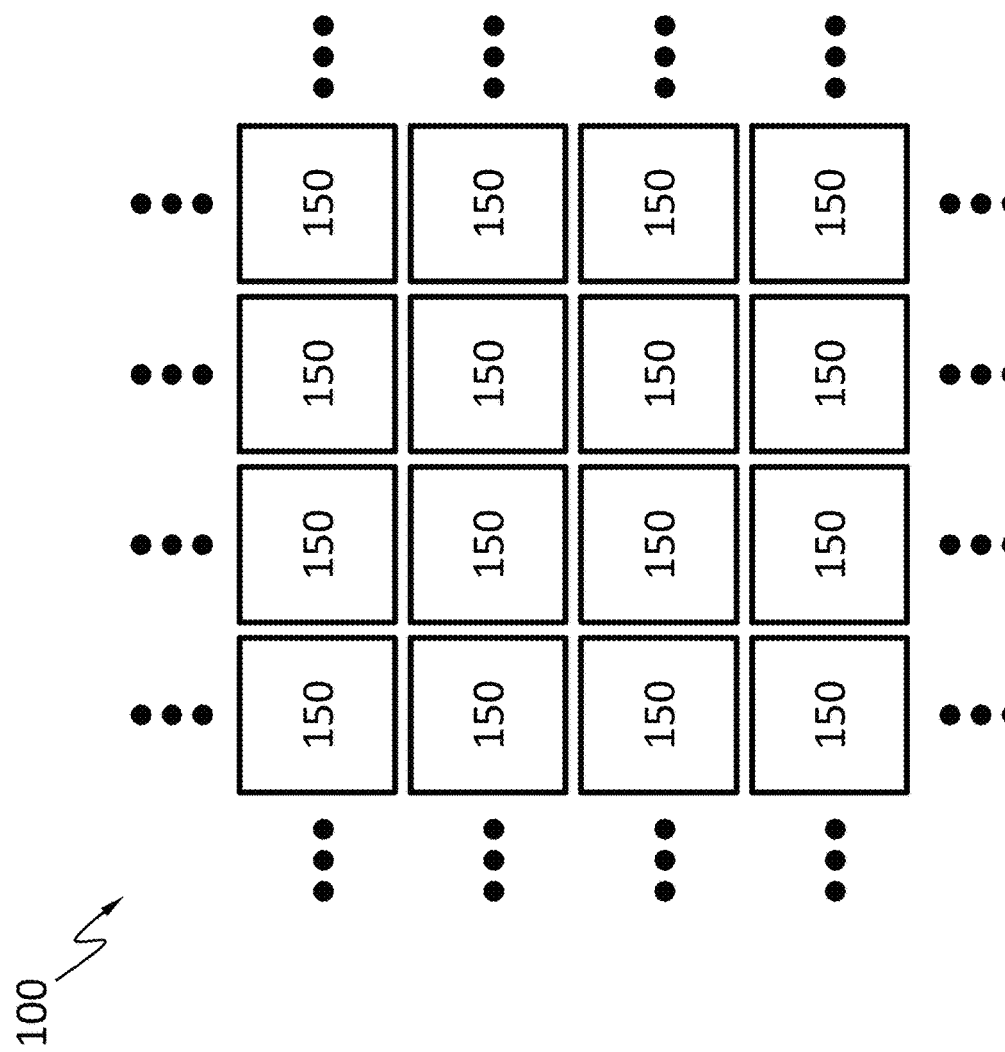
FIG. 3 schematically shows that the device may have an array of pixels, according to an embodiment.

FIG. 3 schematically shows that the radiation detector 100 may have an array of pixels 150. The array may be a rectangular array, a honeycomb array, a hexagonal array or any other suitable array. Each pixel 150 may be configured to detect a radiation particle incident thereon, measure the energy of the radiation particle, or both. For example, each pixel 150 may be configured to count numbers of radiation particles incident thereon whose energy falls in a plurality of bins, within a period of time. All the pixels 150 may be configured to count the numbers of radiation particles incident thereon within a plurality of bins of energy within the same period of time. Each pixel 150 may have its own analog-to-digital converter (ADC) configured to digitize an analog signal representing the energy of an incident radiation particle into a digital signal. The ADC may have a resolution of 10 bits or higher. Each pixel 150 may be configured to measure its dark current, such as before or concurrently with each radiation particle incident thereon. Each pixel 150 may be configured to deduct the contribution of the dark current from the energy of the radiation particle incident thereon. The pixels 150 may be configured to operate in parallel. For example, when one pixel 150 measures an incident radiation particle, another pixel 150 may be waiting for another radiation particle to arrive. The pixels 150 may be but do not have to be individually addressable.

Figure 4B:
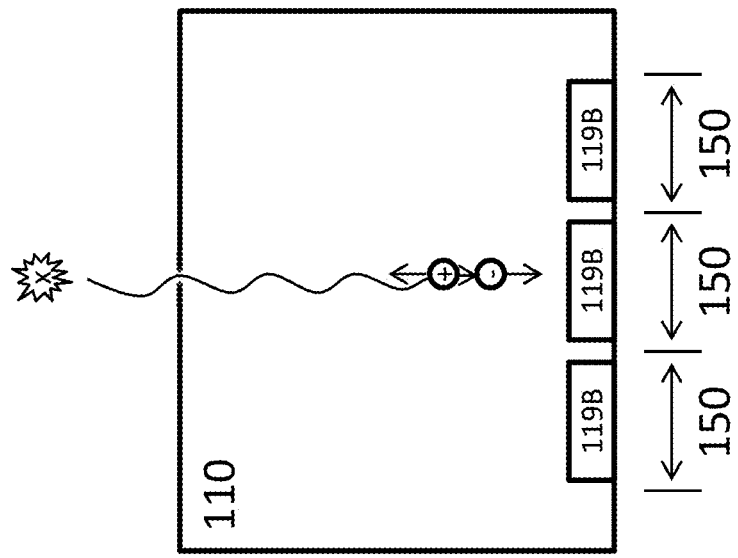
FIG. 4B schematically shows that charge carriers generated in a single pixel when a particle of radiation with an angle of incidence of 0° travels through the radiation absorption layer.
Figure 4A:
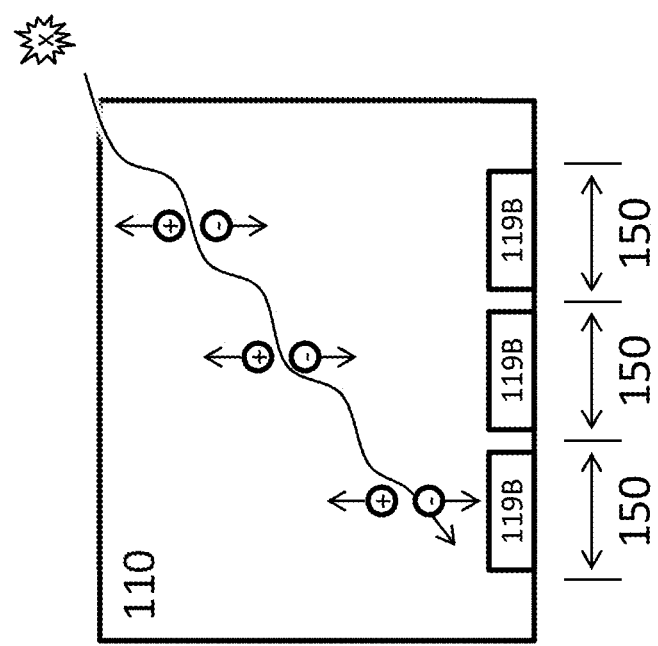
FIG. 4A schematically shows that charge carriers generated in multiple pixels when a particle of radiation with an oblique angle of incidence travels through the radiation absorption layer.

The spatial resolution of the image sensor 9000 may depend on the angle of incidence of the radiation onto the image sensor 9000. The spatial resolution may be lower when the angle of incidence is oblique (e.g., >45°) than the spatial resolution when the angle of incidence is 0°. For example, the spatial resolution at the edges of the image sensor 9000 may be lower than the spatial resolution at the center of the image sensor 9000 when the angle of incidence at the center is 0° and the angles of incidence at the edges are oblique. If the field of view of the image sensor 9000 is large (e.g., 0.5π or larger) or the thickness of the radiation absorption layer 110 in the radiation detectors of the image sensor 9000 is comparable to or larger than the size of the pixels 150, the decrease of the spatial resolution from the center to the edges can be significant. The field of view of the image sensor 9000 is a solid angle through which the image sensor 9000 is sensitive to the radiation. FIG. 4A schematically shows that charge carriers may be generated in the pixels associated with multiple discrete portions of the electric contact 119B when a particle of radiation with an oblique angle of incidence travels through the radiation absorption layer 110. FIG. 4B schematically shows that charge carriers may be generated in the pixel associated with a single discrete portion of the electric contact 119B when a particle of radiation with an angle of incidence of 0° travels through the radiation absorption layer 110.

Figure 5:
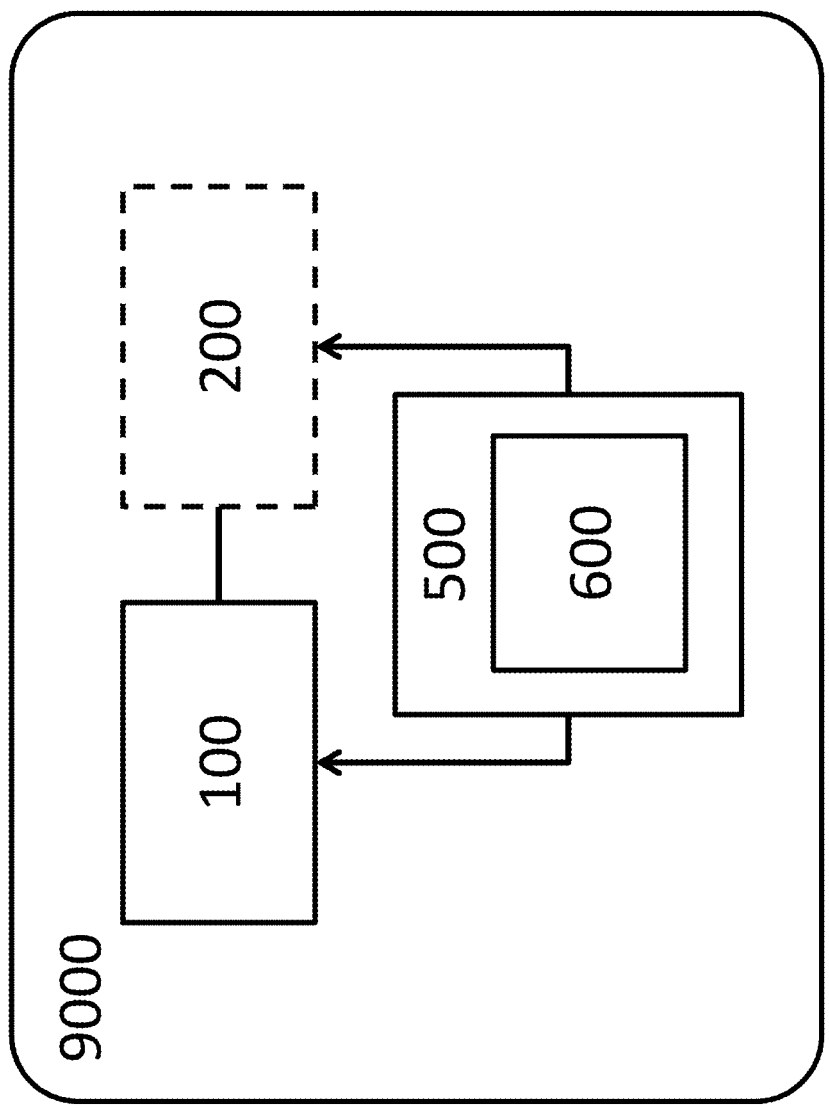
FIG. 5 schematically shows a functional block diagram of the image sensor, according to an embodiment.

In an embodiment, the radiation detectors 100 (e.g., 100A and 100B) of the image sensor 9000 can move to multiple positions, relative to the radiation source 109. The image sensor 9000 may use the radiation detectors 100 and with the radiation from the radiation source 109 to capture images of multiple portions of the scene 50 respectively at the multiple positions. The image sensor 9000 can stitch these images to form an image of the entire scene 50. As shown in FIG. 5, according to an embodiment, the image sensor 9000 may include an actuator 500 configured to move the radiation detectors 100 to the multiple positions. The actuator 500 may include a controller 600. The image sensor may include a collimator 200 that only allows radiation to reach active area of the radiation detectors 100. Active areas of the radiation detectors 100 are areas of the radiation detectors 100 that are sensitive to the radiation. The actuator 500 may move the collimator 200 together with the radiation detectors 100. The positions may be determined by the controller 600.

Figure 6A:
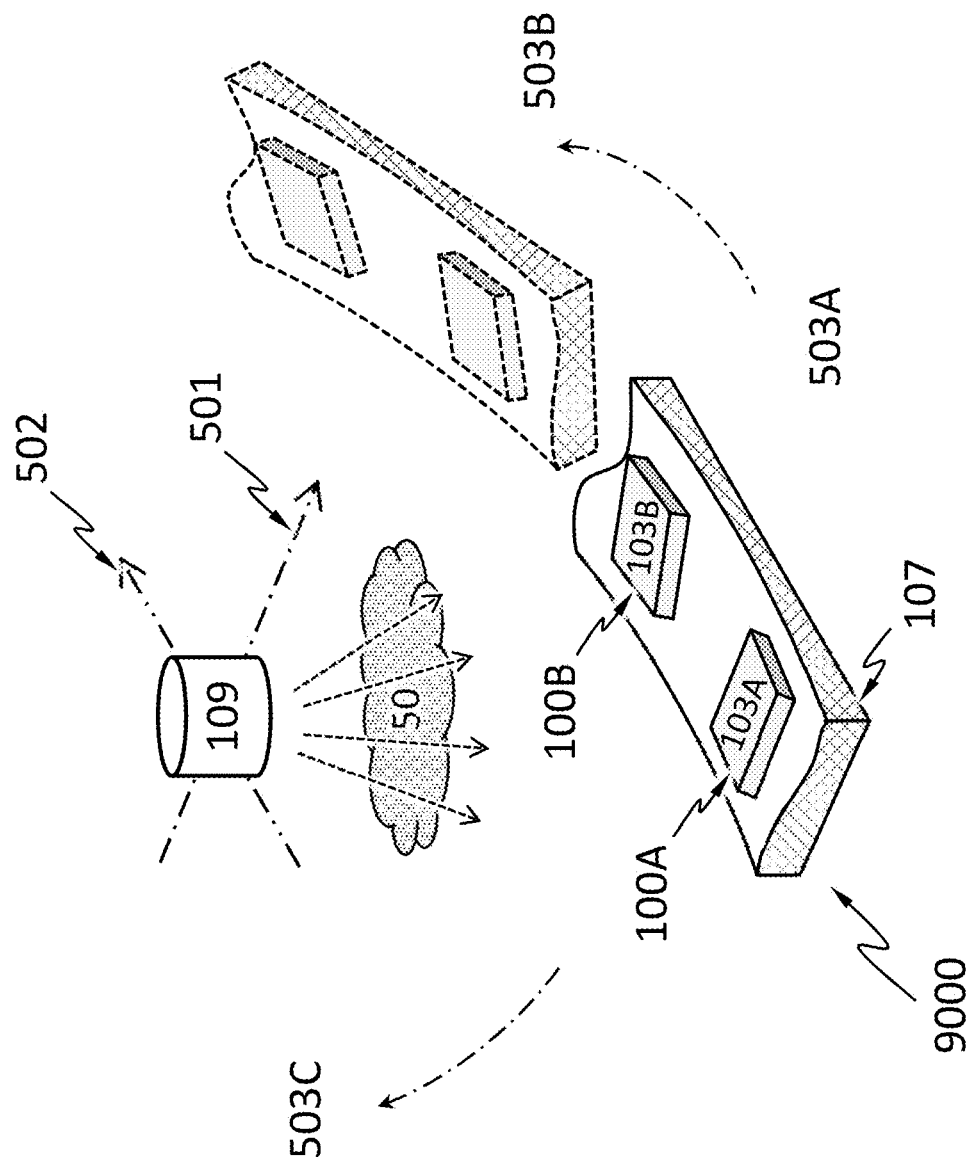
FIG. 6A and FIG. 6B each schematically shows movements of detectors of the image sensor relative to a radiation source, according to an embodiment.
Figure 6B:
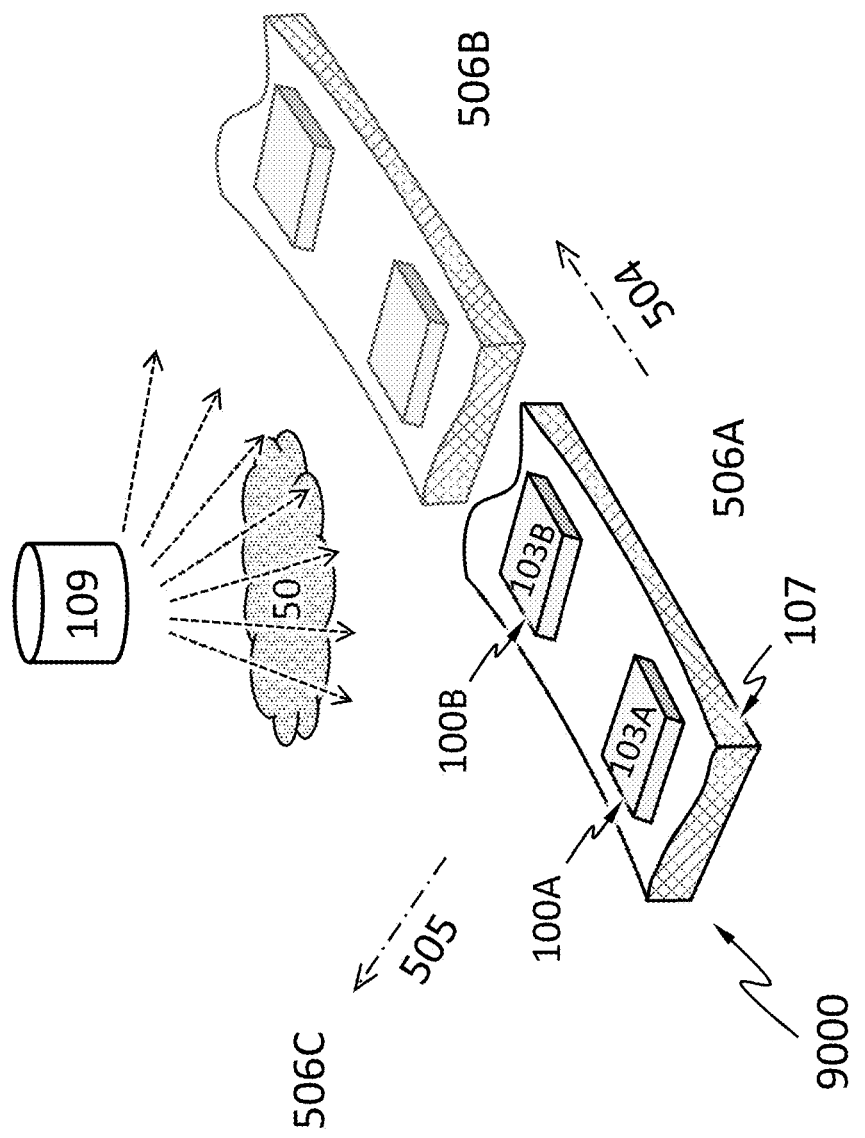

FIG. 6A and FIG. 6B each schematically shows movements of the radiation detectors 100 (e.g., 100A and 100B) relative to the radiation source 109, according to an embodiment. In the examples of FIG. 6A and FIG. 6B, only a portion of the image sensor 9000 with the first radiation detector 100A and the second radiation detector 100B is shown. The first radiation detector 100A and the second radiation detector 100B may be arranged on the support 107. A relative position of the first radiation detector 100A with respect to the second radiation detector 100B remains the same at the multiple positions. The relative position of the first radiation detector 100A with respect to the second radiation detector 100B may but does not necessarily remain the same while they move from one of the multiple positions to another. The first radiation detector 100A and the second radiation detector 100B may rotate about a first axis 501, relative to the radiation source 109. As shown in the example of FIG. 6A, the first radiation detector 100A and the second radiation detector 100B rotate from position 503A to position 503B about the first axis 501, relative to the radiation source 109. The first axis 501 may be parallel to the first planar surface 103A of the first radiation detector 100A and the second planar surface 103B of the second radiation detector 100B. The radiation source may be on the first axis 501. The first radiation detector 100A and the second radiation detector 100B may rotate about a second axis 502 relative to the radiation source 109. The second axis 502 is different from the first axis 501. For example, the second axis 502 may be perpendicular to the first axis 501. As shown in the example of FIG. 6A, the first radiation detector 100A and the second radiation detector 100B can rotate from position 503A to position 503C, about the second axis 502. The radiation source 109 may be on the second axis 502.

As shown in the example of FIG. 6B, the first radiation detector 100A and the second radiation detector 100B translate along a first direction 504 from position 506A to position 506B, relative to the radiation source 109. The first radiation detector 100A and the second radiation detector 100B may translate along a second direction 505. The second direction 505 is different from the first direction 504. For example, the second direction 505 may be perpendicular to the first direction 504. As shown in the example of FIG. 6B, the first radiation detector 100A and the second radiation detector 100B can translate from position 506A to position 506C, along the second direction 505. The first direction 504 or the second direction 505 may be parallel to both, either or neither of the first planar surface 103A and the second planar surface 103B. For example, the first direction 504 may be parallel to the first planar surface 103A, but not parallel to the second planar surface 103B.

In the examples of FIG. 6A and FIG. 6B, the positions and orientations of the radiation source 109 remain the same during rotation or translation.

Figure 7B:
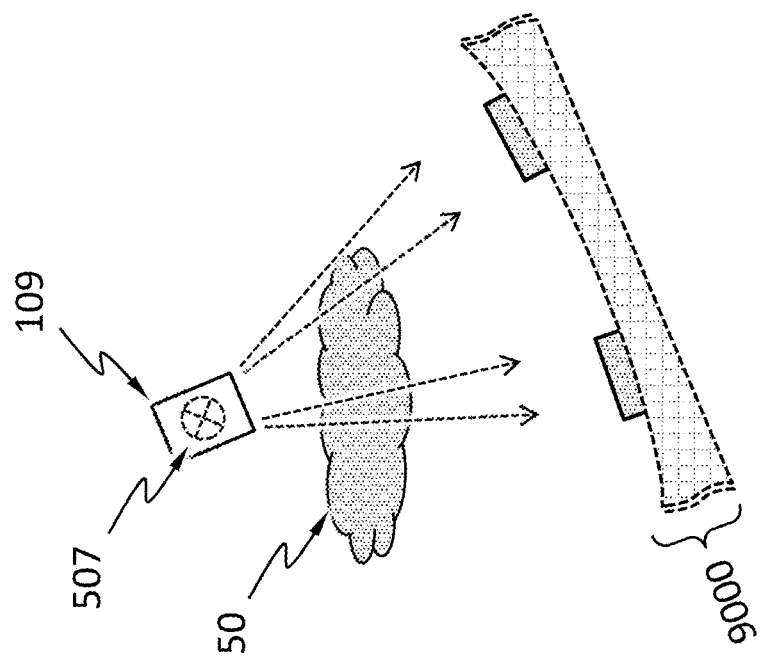
FIG. 7A and FIG. 7B each schematically shows rotations of the imaging system relative to a scene about a third axis passing through the radiation source, according to an embodiment.
Figure 7A:
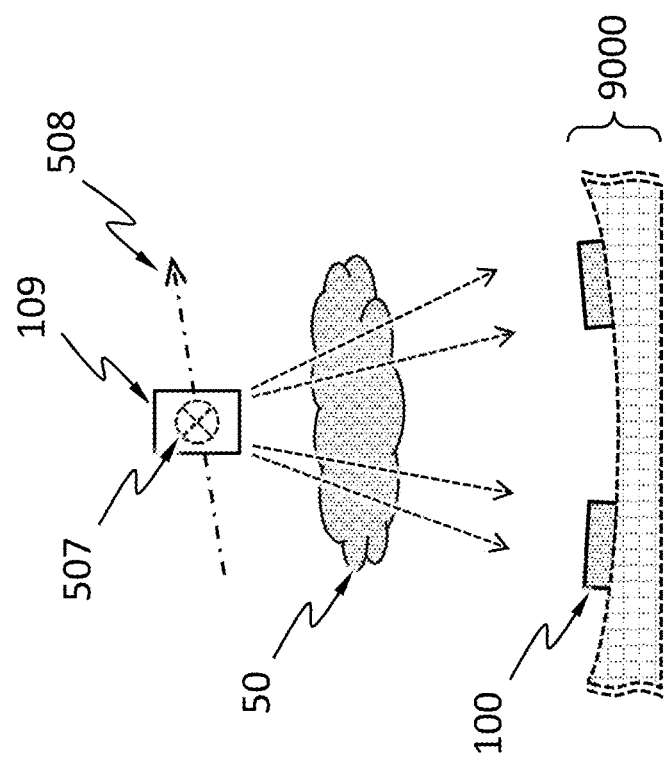

The radiation source 109 and the image sensor 9000 included in the system 1000 may be configured to rotate together relative to the scene 50. According to one embodiment shown in FIG. 7A and FIG. 7B, the radiation source 109 is on a third axis 507, and the third axis 507 is perpendicular to the page of FIG. 7A and FIG. 7B. FIG. 7A schematically shows the initial positions of the radiation source 109 and the image sensor 9000 before a rotation about the third axis 507. FIG. 7B schematically shows positions of the radiation source 109 and the image sensor 9000 after the rotation. A relative position of the radiation source 109 with respect to the image sensor 9000 remains the same, a position and an orientation of the scene 50 remain the same during the rotation. After the rotation, the radiation may pass through the scene 50 along different directions and may be detected by the image sensor 9000 with different angles of incidence.

According to one embodiment, the radiation source 109 and the image sensor 9000 included in the imaging system 1000 are configured to rotate about a fourth axis 508 which is different from the third axis 507, as shown in FIG. 7A. The fourth axis 508 may be perpendicular to the third axis 507 or may be following other directions. The radiation source 109 may be on the fourth axis 508.

Figure 8B:
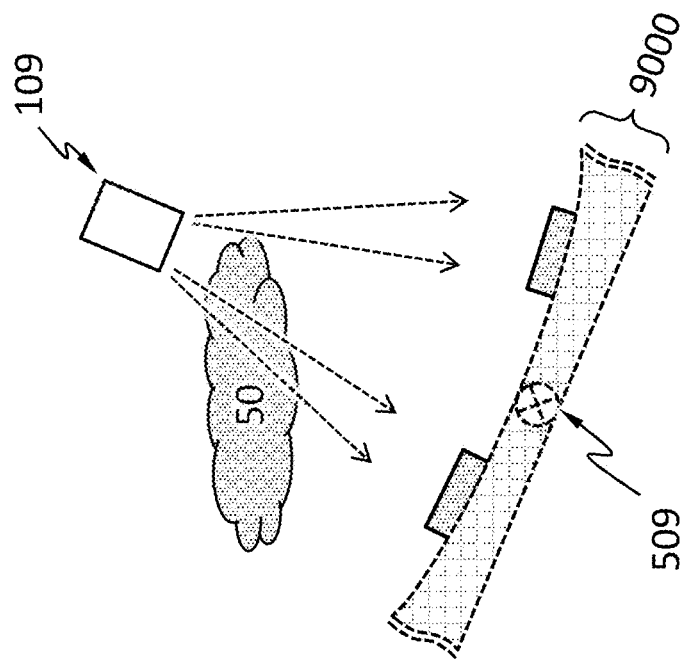
FIG. 8A and FIG. 8B each schematically shows rotations of the imaging system relative to a scene about a third axis passing through the image sensor, according to an embodiment.
Figure 8A:
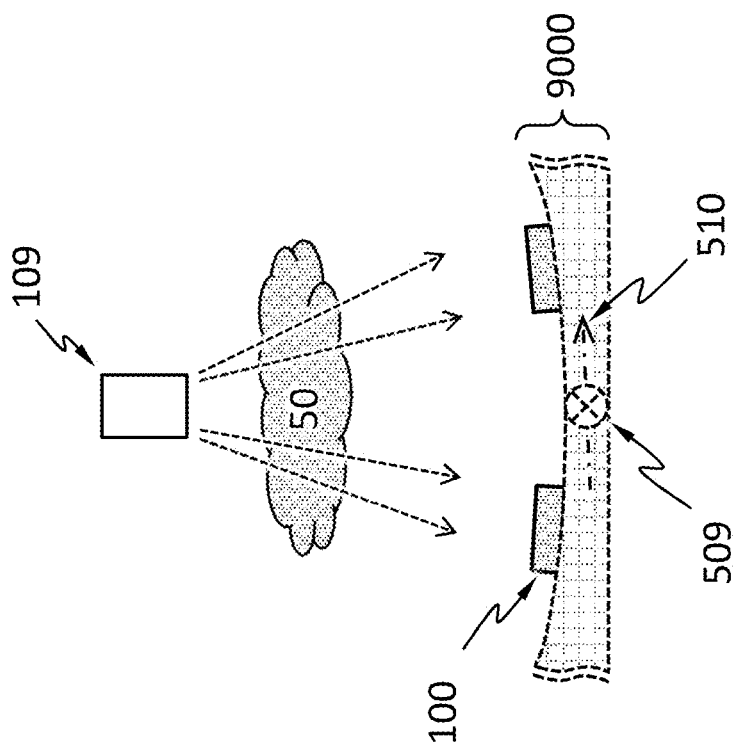

According to one embodiment shown in FIG. 8A and FIG. 8B, the image sensor 9000 is on a third axis 509, and the third axis 509 is perpendicular to the page of FIG. 8A and FIG. 8B. FIG. 8A schematically shows the initial positions of the radiation source 109 and the image sensor 9000 before a rotation about the third axis 509. FIG. 8B schematically shows positions of the radiation source 109 and the image sensor 9000 after the rotation. A relative position of the radiation source 109 with respect to the image sensor 9000 remains the same, a position and an orientation of the scene 50 remain the same during the rotation. After the rotation, the radiation may pass through the scene 50 along different directions and may be detected by the image sensor 9000 with different angles of incidence.

According to one embodiment, the imaging system 1000 are configured to rotate about a fourth axis 510 which is different from the third axis 509, as shown in FIG. 8A. The fourth axis 510 may be perpendicular to the third axis 509 or may be following other directions. The radiation source may be on the fourth axis 510.

FIG. 9 schematically shows that the image sensor 9000 can capture images of portions of the scene 50. In the example shown in FIG. 9, the radiation detectors 100 move to three positions A, B and C, for example, by using the actuator 500. Respectively at the positions A, B and C, the image sensor 9000 captures images 51A, 51B and 51C of portions of the scene 50. The image sensor 9000 can stitch the images 51A, 51B and 51C of the portions to form an image of the scene 50. The images 51A, 51B and 51C of the portions may have overlap among one another to facilitate stitching. Every portion of the scene 50 may be in at least one of the images captured when the detectors are at the multiple positions. Namely, the images of the portions when stitched together may cover the entire scene 50.

The radiation detectors 100 may be arranged in a variety of ways in the image sensor 9000. FIG. 10A schematically shows one arrangement, according to an embodiment, where the radiation detectors 100 are arranged in staggered rows. For example, radiation detectors 100A and 100B are in the same row, aligned in the Y direction, and uniform in size; radiation detectors 100C and 100D are in the same row, aligned in the Y direction, and uniform in size. Radiation detectors 100A and 100B are staggered in the X direction with respect to radiation detectors 100C and 100D. According to an embodiment, a distance X2 between two neighboring radiation detectors 100A and 100B in the same row is greater than a width X1 (i.e., dimension in the X direction, which is the extending direction of the row) of one radiation detector in the same row and is less than twice the width X1. Radiation detectors 100A and 100E are in a same column, aligned in the X direction, and uniform in size; a distance Y2 between two neighboring radiation detectors 100A and 100E in the same column is less than a width Y1 (i.e., dimension in the Y direction) of one radiation detector in the same column. This arrangement allows imaging of the scene as shown in FIG. 9, and an image of the scene may be obtained from stitching three images of portions of the scene captured at three positions spaced apart in the X direction.

Figure 10B:
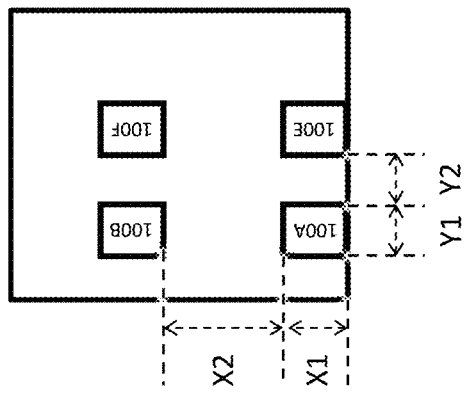
FIG. 10A-FIG. 10C schematically show arrangements of the detectors in the image sensor, according to some embodiments.
Figure 10A:
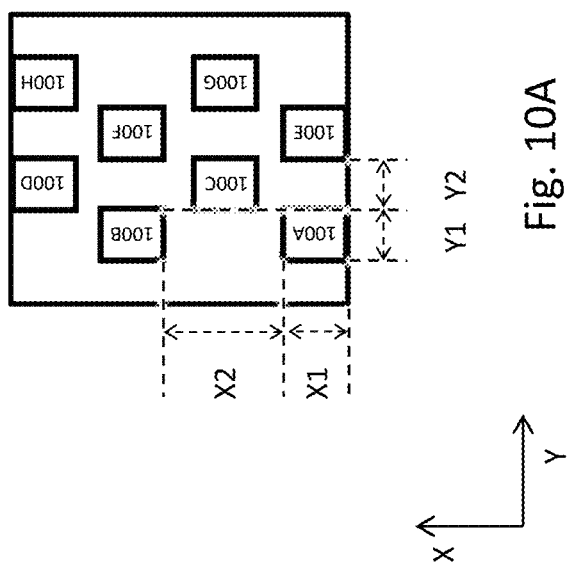

FIG. 10B schematically shows another arrangement, according to an embodiment, where the radiation detectors 100 are arranged in a rectangular grid. For example, the radiation detectors 100 may include radiation detectors 100A, 100B, 100E and 100F as arranged exactly in FIG. 10A, without radiation detectors 100C, 100D, 100G, or 100H in FIG. 10A. This arrangement allows imaging of the scene by taking images of portions of the scene at six positions. For example, three positions spaced apart in the X direction and another three positions spaced apart in the X direction and spaced apart in the Y direction from the first three positions.

Figure 10C:
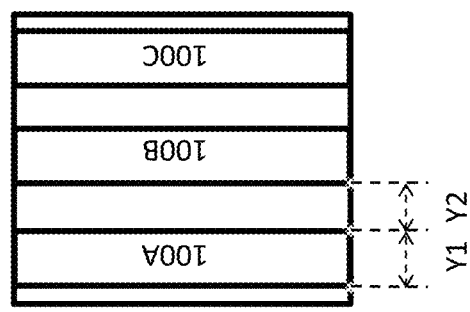

Other arrangements may also be possible. For example, in FIG. 10C, the radiation detectors 100 may span the whole width of the image sensor 9000 in the X-direction, with a distance Y2 between two neighboring radiation detectors 100 being less than a width of one radiation detector Y1. Assuming the width of the detectors in the X direction is greater than the width of the scene in the X direction, the image of the scene may be stitched from two images of portions of the scene captured at two positions spaced apart in the Y direction.

Figure 11:
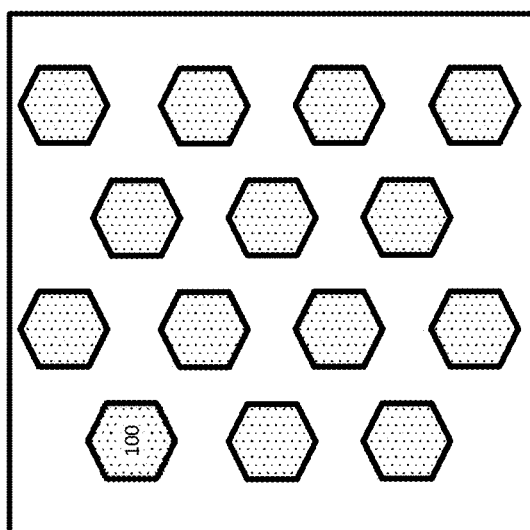
FIG. 11 schematically shows an image sensor with plurality of detectors that are hexagonal in shape, according to an embodiment.

The radiation detectors 100 described above may be provided with any suitable size and shapes. According to an embodiment (e.g., in FIG. 9), at least some of the radiation detectors are rectangular in shape. According to an embodiment, as shown in FIG. 11, at least some of the radiation detectors are hexagonal in shape.

Figure 12:
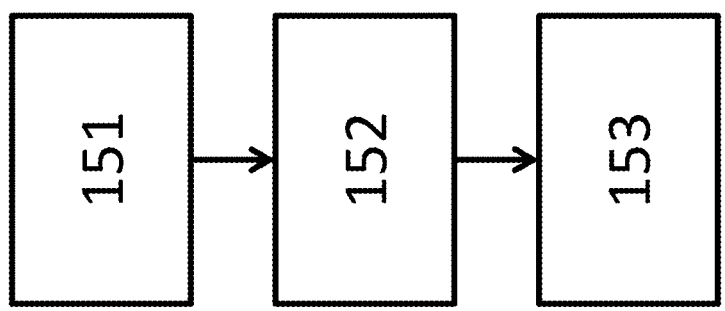
FIG. 12 schematically shows a flowchart for a method of forming an image of a scene by stitching images of multiple portions of the scene captured at multiple positions, according to an embodiment.

FIG. 12 schematically shows a flowchart for a method, according to an embodiment. In procedure 151, a first image of a first portion of the scene 50 is formed, by using the image sensor 9000, while the imaging system 1000 is at a first rotational position relative to the scene 50. In procedure 152, the imaging system 1000 is rotated relative to the scene 50 about a third axis (e.g., 507 or 509) to a second rotational position relative to the scene 50. The system 1000 may rotate about the third axis 507 which may pass through the radiation source 109, or the system 1000 may rotate about the third axis 509 which may pass through the image sensor 9000. In procedure 153, a second image of a second portion of the scene 50 is formed by using the image sensor 9000, while the imaging system 1000 is at the second rotational position relative to the scene 50. According to an embodiment, the method may comprise rotating the system 1000 relative to the scene 50 about a fourth axis (e.g., 508, or 510) (different from the third axis (e.g., 507, or 509)) to a third rotational position relative to the scene 50 and forming a third image of the scene 50 with the image sensor 9000 while the system 1000 is at the third rotational position relative to the scene 50. The radiation source 109 or the image sensor 9000 may be on the fourth axis.

The imaging system 1000 described above may be used in various systems such as those provided below.

Figure 13:
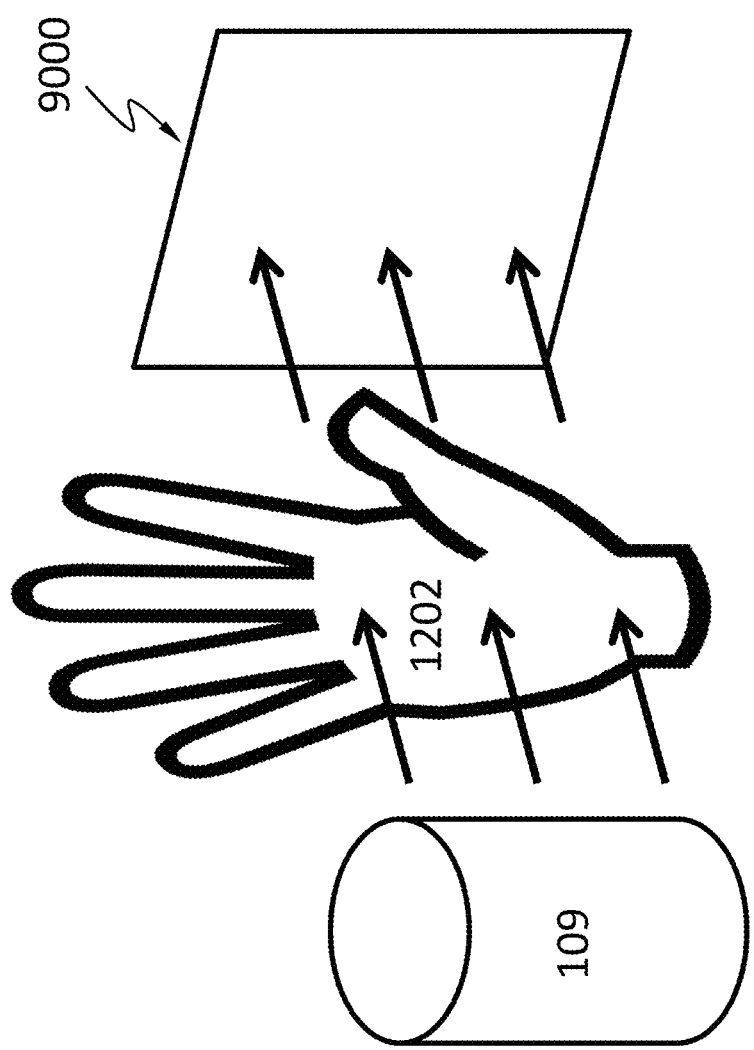
FIG. 13 schematically shows a system comprising the image sensor described herein, suitable for medical imaging such as chest radiation radiography, abdominal radiation radiography, etc., according to an embodiment FIG. 14 schematically shows a system comprising the image sensor described herein suitable for dental radiation radiography, according to an embodiment.

FIG. 13 schematically shows a system comprising the imaging system 1000 as described in relation to FIG. 1-FIG. 11. The system may be used for medical imaging such as chest radiation radiography, abdominal radiation radiography, etc. Radiation emitted from the radiation source 109 penetrates an object 1202 (e.g., a human body part such as chest, limb, abdomen), is attenuated by different degrees by the internal structures of the object 1202 (e.g., bones, muscle, fat and organs, etc.), and is projected to the image sensor 9000. The image sensor 9000 forms an image by detecting the intensity distribution of the radiation.

Figure 14:
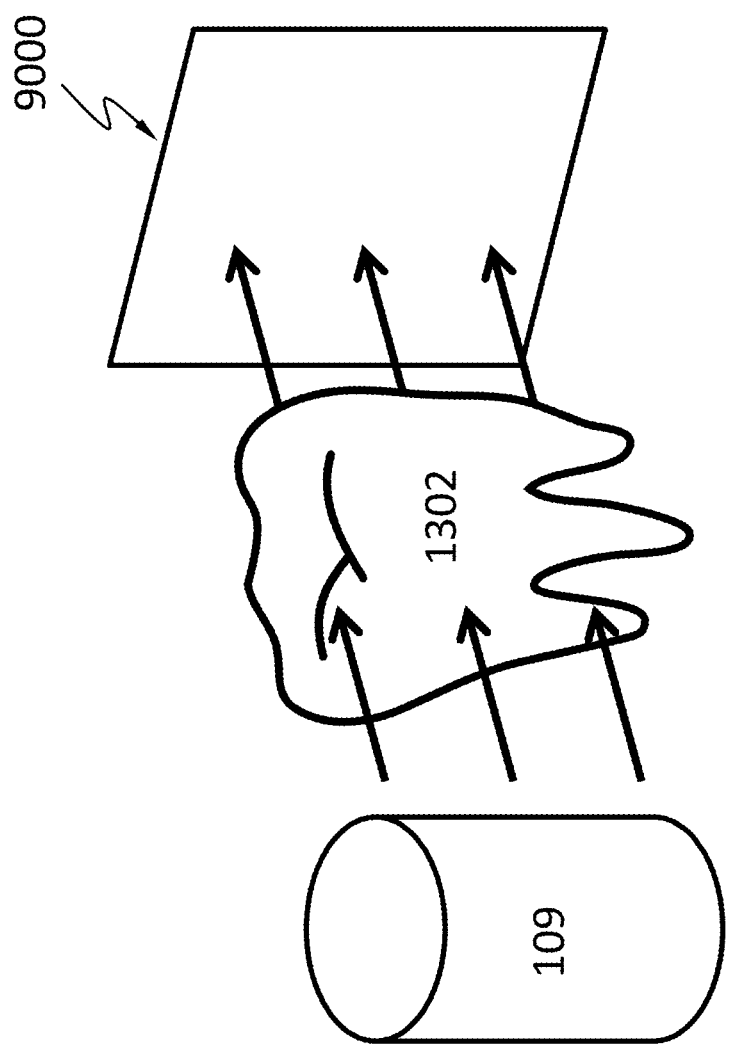

FIG. 14 schematically shows a system comprising the imaging system 1000 as described in relation to FIG. 1-FIG. 11. The system may be used for medical imaging such as dental radiation radiography. Radiation emitted from the radiation source 109 penetrates an object 1302 that is part of a mammal (e.g., human) mouth. The object 1302 may include a maxilla bone, a palate bone, a tooth, the mandible, or the tongue. The radiation is attenuated by different degrees by the different structures of the object 1302 and is projected to the image sensor 9000. The image sensor 9000 forms an image by detecting the intensity distribution of the radiation. Teeth absorb radiation more than dental caries, infections, periodontal ligament. The dosage of radiation received by a dental patient is typically small (around 0.150 mSv for a full mouth series).

Figure 15:
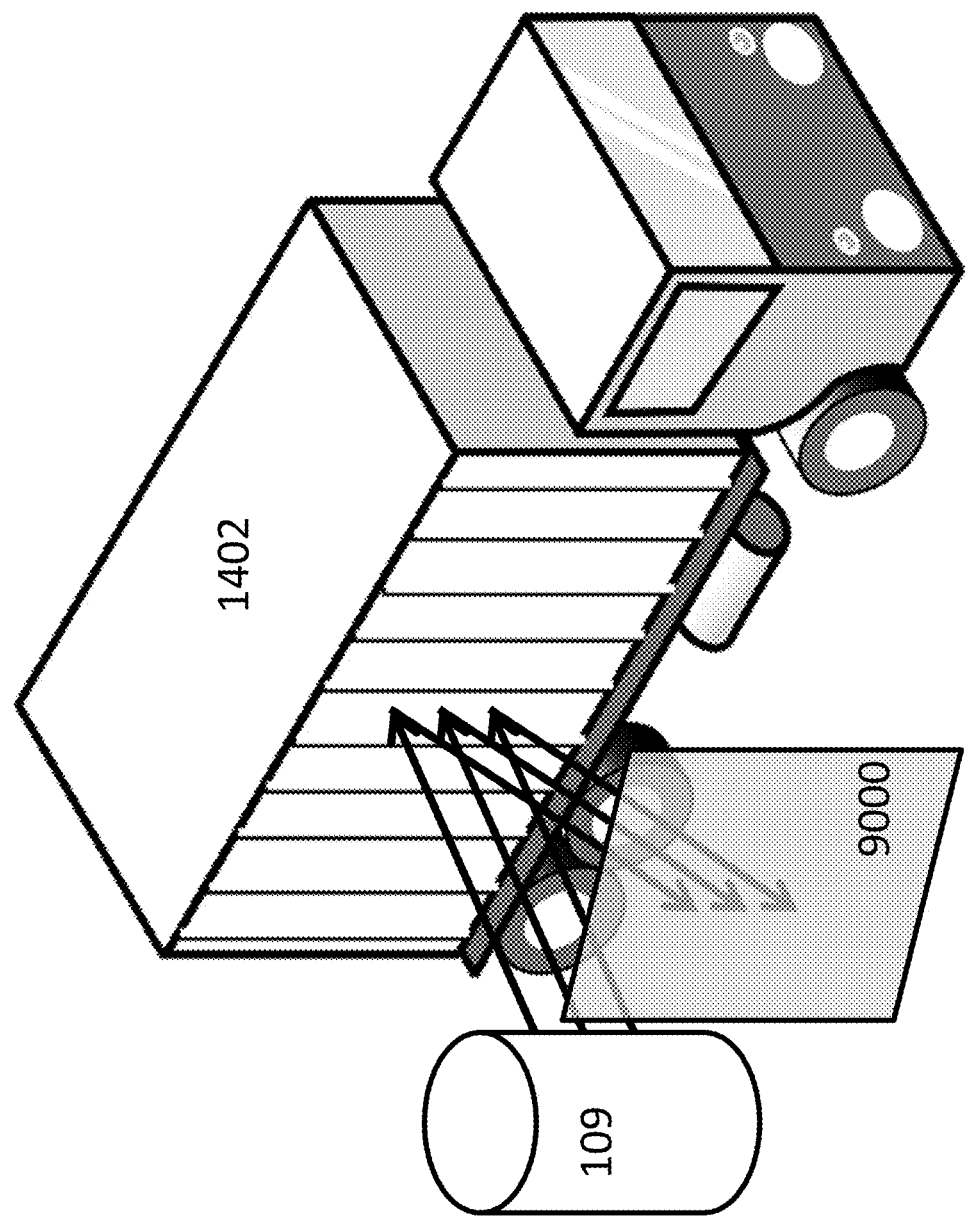
FIG. 15 schematically shows a cargo scanning or non-intrusive inspection (NII) system comprising the image sensor described herein, according to an embodiment.

FIG. 15 schematically shows a cargo scanning or non-intrusive inspection (NII) system comprising the imaging system 1000 as described in relation to FIG. 1-FIG. 11. The system may be used for inspecting and identifying goods in transportation systems such as shipping containers, vehicles, ships, luggage, etc. Radiation emitted from the radiation source 109 may backscatter from an object 1402 (e.g., shipping containers, vehicles, ships, etc.) and be projected to the image sensor 9000. Different internal structures of the object 1402 may backscatter radiation differently. The image sensor 9000 forms an image by detecting the intensity distribution of the backscattered radiation and/or energies of the backscattered radiation particles.

Figure 16:
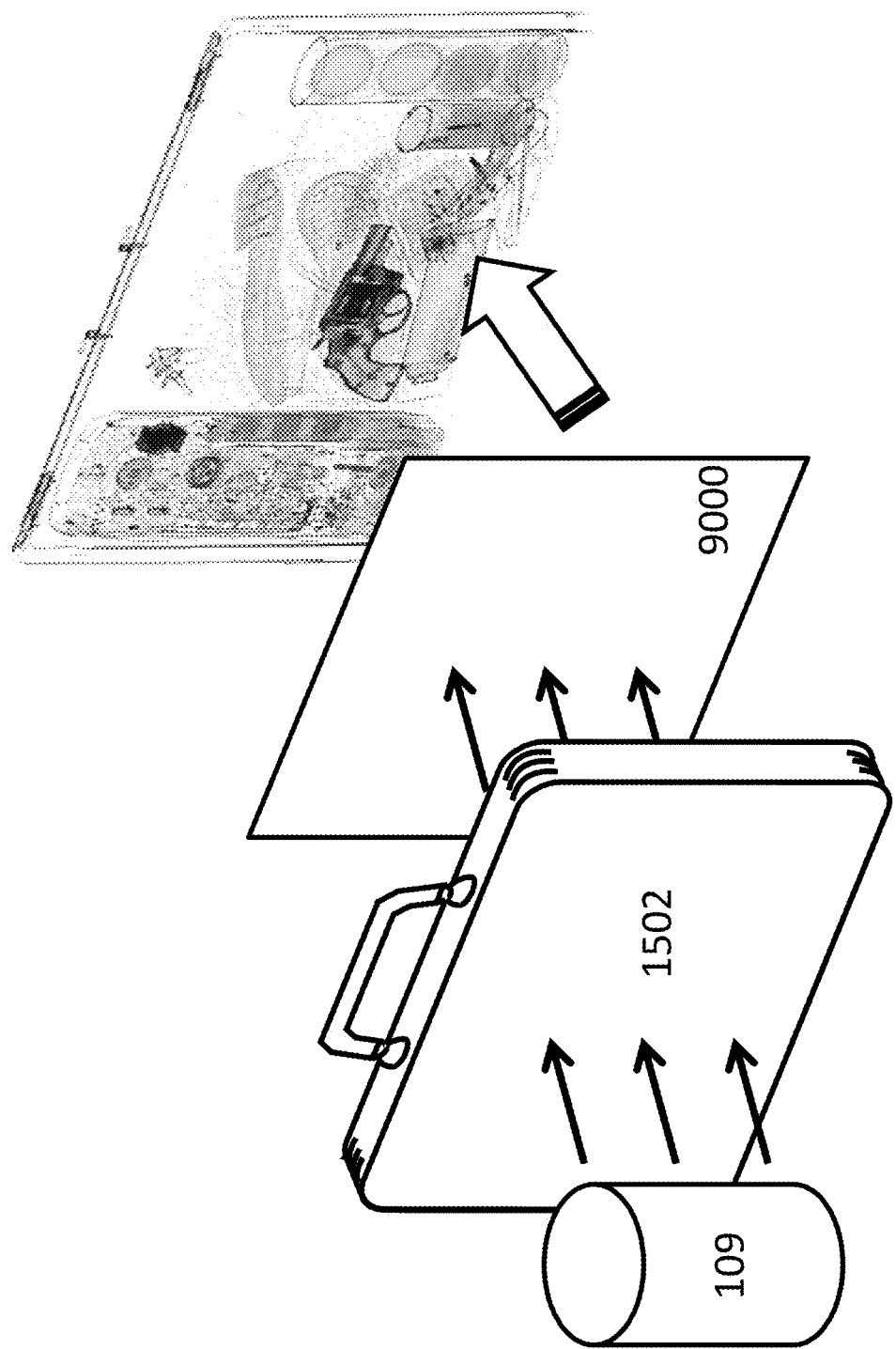
FIG. 16 schematically shows another cargo scanning or non-intrusive inspection (NII) system comprising the image sensor described herein, according to an embodiment.

FIG. 16 schematically shows another cargo scanning or non-intrusive inspection (NII) system comprising the imaging system 1000 as described in relation to FIG. 1-FIG. 11. The system may be used for luggage screening at public transportation stations and airports. Radiation emitted from the radiation source 109 may penetrate a piece of luggage 1502, be differently attenuated by the contents of the luggage, and projected to the image sensor 9000. The image sensor 9000 forms an image by detecting the intensity distribution of the transmitted radiation. The system may reveal contents of luggage and identify items forbidden on public transportation, such as firearms, narcotics, edged weapons, flammables.

Figure 17:
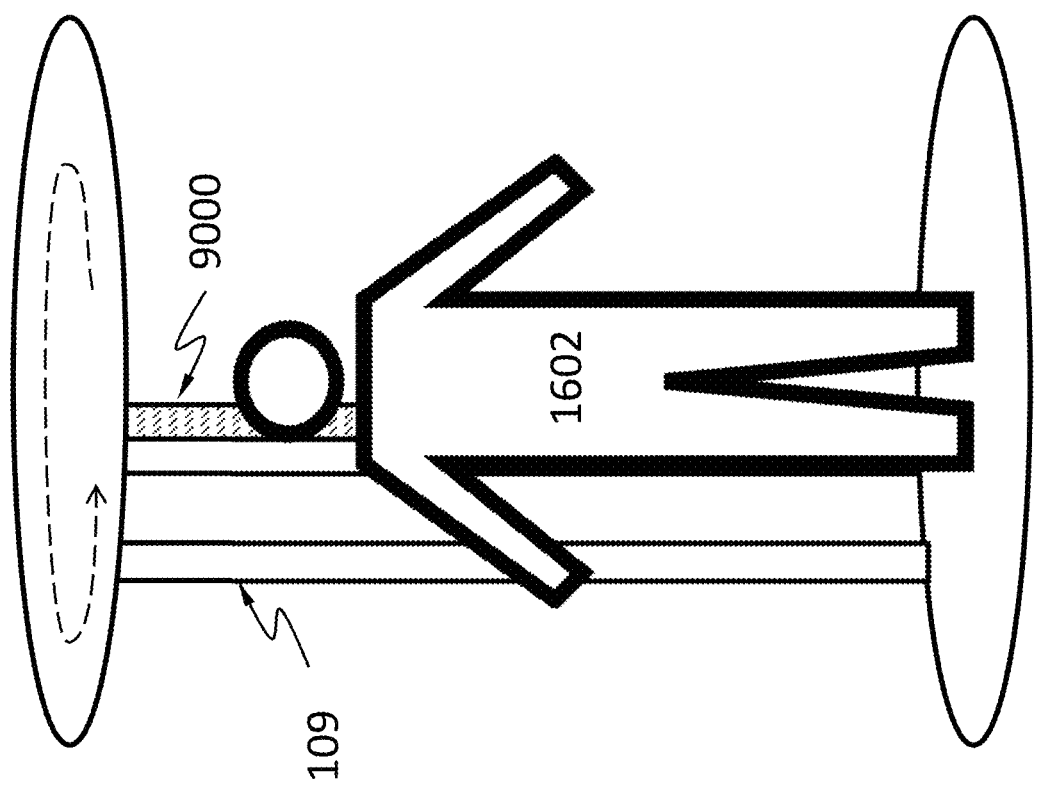
FIG. 17 schematically shows a full-body scanner system comprising the image sensor described herein, according to an embodiment.

FIG. 17 schematically shows a full-body scanner system comprising the imaging system 1000 as described in relation to FIG. 1-FIG. 11. The full-body scanner system may detect objects on a person's body for security screening purposes, without physically removing clothes or making physical contact. The full-body scanner system may be able to detect non-metal objects. Radiation emitted from the radiation source 109 may backscatter from a human 1602 being screened and objects thereon, and be projected to the image sensor 9000. The objects and the human body may backscatter radiation differently. The image sensor 9000 forms an image by detecting the intensity distribution of the backscattered radiation. The image sensor 9000 and the radiation source 109 may be configured to scan the human in a linear or rotational direction.

Figure 18:
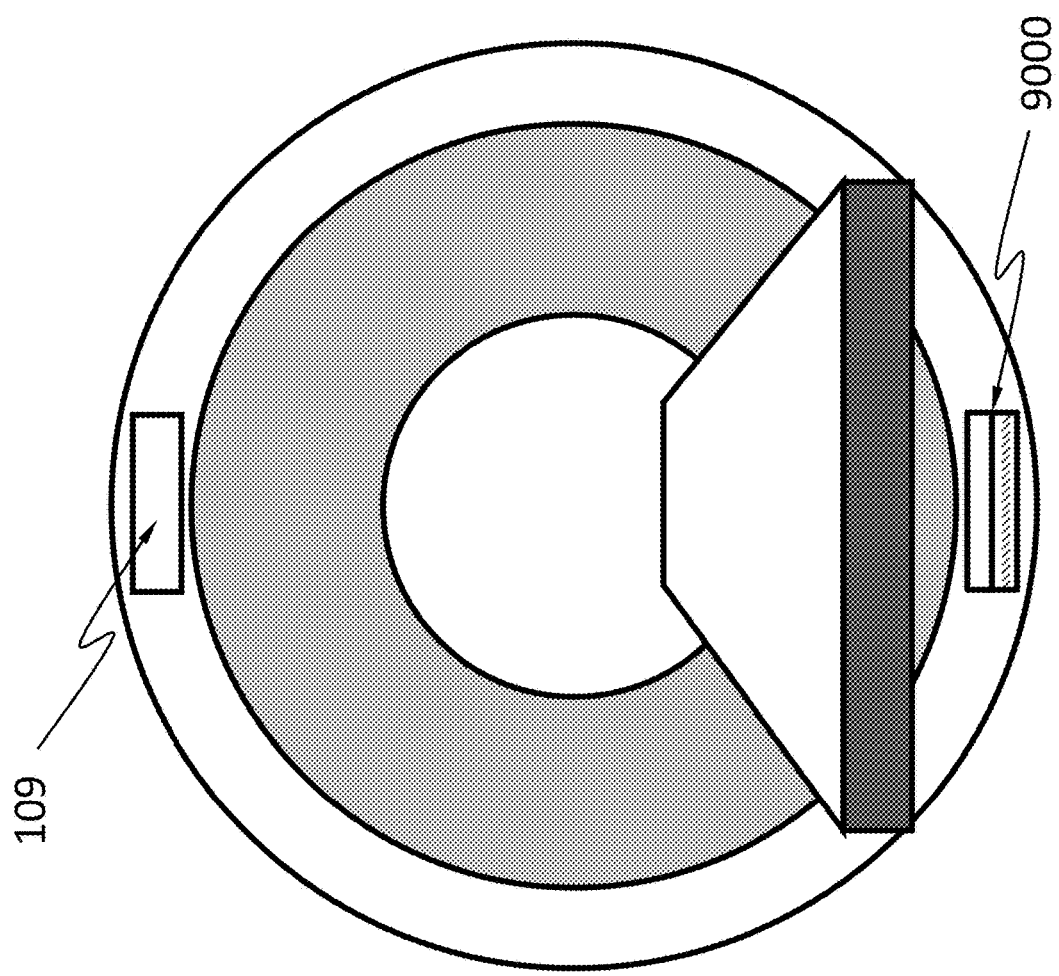
FIG. 18 schematically shows a radiation computed tomography (Radiation CT) system comprising the image sensor described herein, according to an embodiment.

FIG. 18 schematically shows a radiation computed tomography (Radiation CT) system. The Radiation CT system uses computer-processed radiations to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The Radiation CT system comprises the image sensor 9000 as described in relation to FIG. 1-FIG. 11. The image sensor 9000 and the radiation source 109 may be configured to rotate synchronously along one or more circular or spiral paths.

Figure 19:
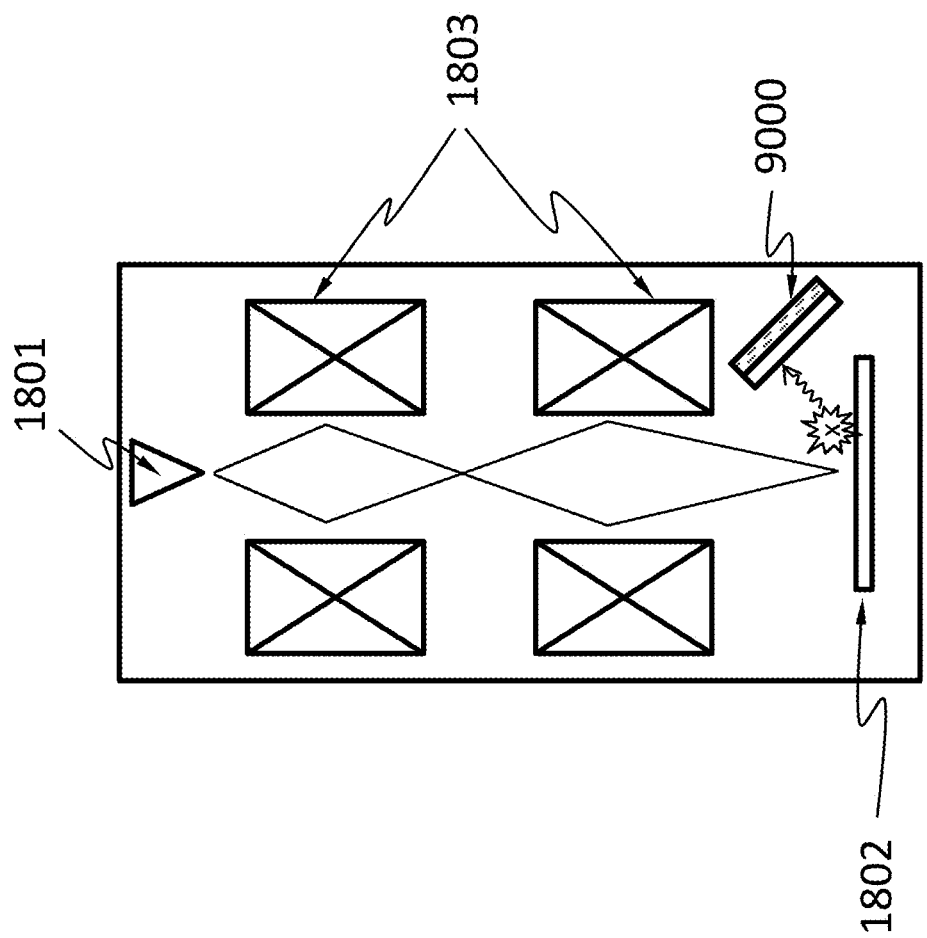
FIG. 19 schematically shows an electron microscope comprising the image sensor described herein, according to an embodiment.

FIG. 19 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the image sensor 9000 as described in relation to FIG. 1-FIG. 11, for performing energy-dispersive radiation spectroscopy (EDS). EDS is an analytical technique used for the elemental analysis or chemical characterization of a sample. When the electrons incident on a sample, they cause emission of characteristic radiations from the sample. Namely, the sample functions as the radiation source 109 in this example. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of radiation. The number and energy of the radiations emitted from the sample can be measured by the image sensor 9000.

The imaging system 1000 described here may have other applications such as in a radiation telescope, radiation mammography, industrial radiation defect detection, radiation microscopy or microradiography, radiation casting inspection, radiation non-destructive testing, radiation weld inspection, radiation digital subtraction angiography, etc. It may be suitable to use the imaging system 1000 in place of a photographic plate, a photographic film, a PSP plate, a radiation image intensifier, a scintillator, or another semiconductor radiation detector.

Figure 20A:
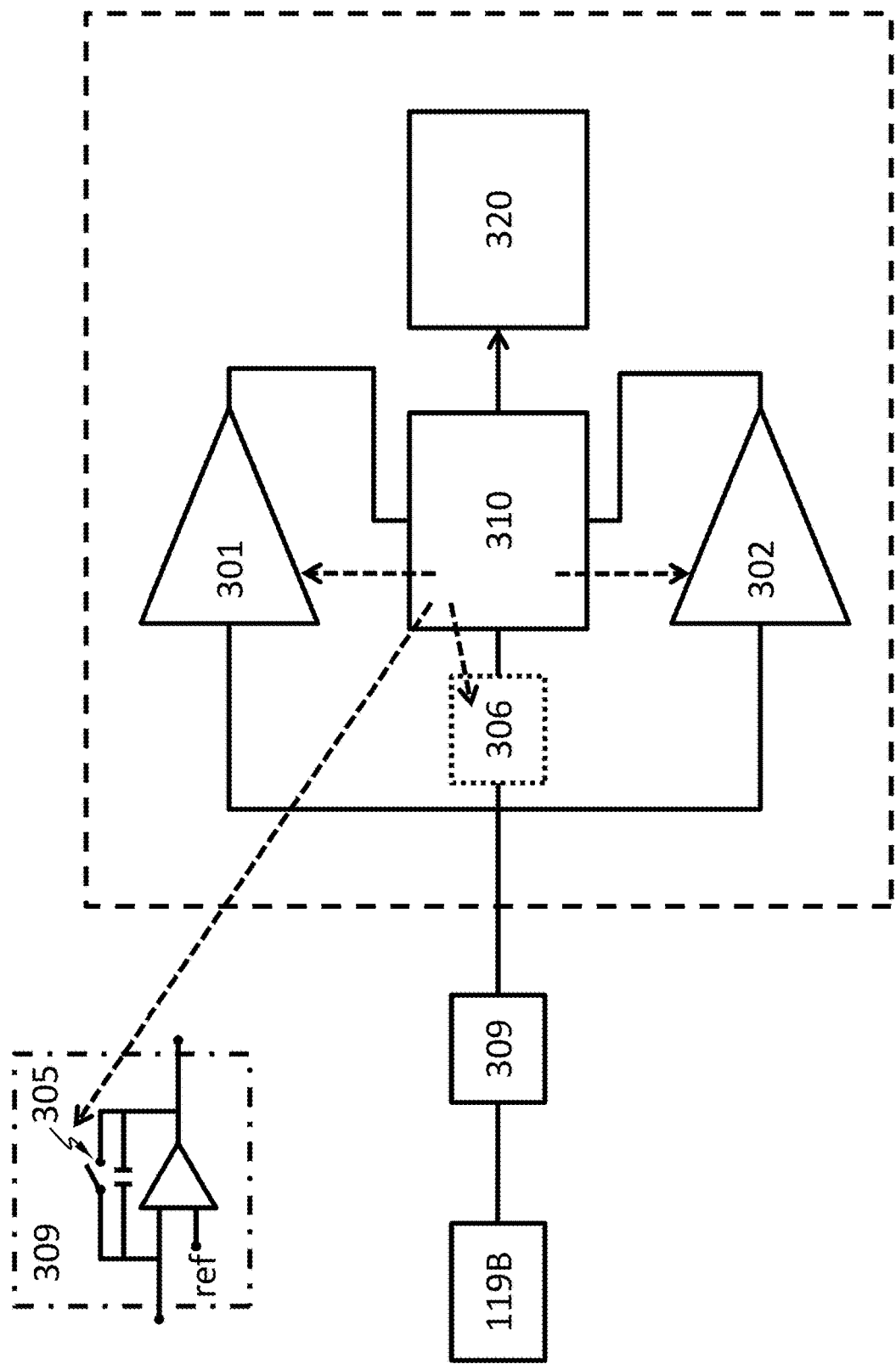
FIG. 20A and FIG. 20B each show a component diagram of an electronic system of the radiation detector in FIG. 2A, FIG. 2B and FIG. 2C, according to an embodiment.
Figure 20B:
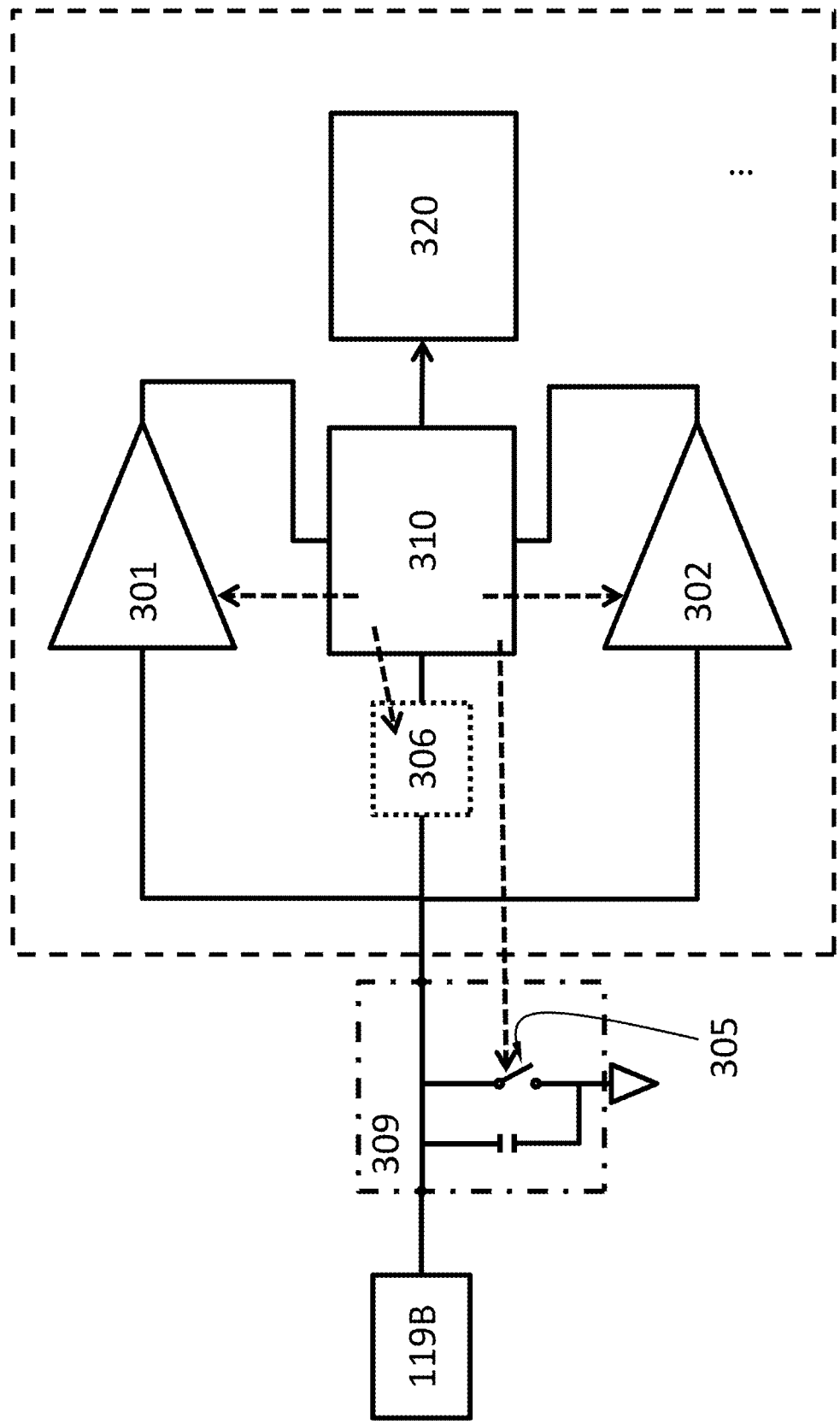

FIG. 20A and FIG. 20B each show a component diagram of the electronic system 121, according to an embodiment. The electronic system 121 may include a first voltage comparator 301, a second voltage comparator 302, a counter 320, a switch 305, an optional voltmeter 306 and a controller 310.

The first voltage comparator 301 is configured to compare the voltage of at least one of the electric contacts 119B to a first threshold. The first voltage comparator 301 may be configured to monitor the voltage directly, or calculate the voltage by integrating an electric current flowing through the electric contact 119B over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator. The first threshold may be 5-10%, 10%-20%, 20-30%, 30-40% or 40-50% of the maximum voltage one incident particle of radiation may generate on the electric contact 119B. The maximum voltage may depend on the energy of the incident particle of radiation, the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electric contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, \text{if } x \geq 0 \\ -x, \text{if } x \leq 0 \end{cases}.$$

The second threshold may be 200%-300% of the first threshold. The second threshold may be at least 50% of the maximum voltage one incident particle of radiation may generate on the electric contact 119B. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the electronic system 121 to operate under a high flux of incident particles of radiation. However, having a high speed is often at the cost of power consumption.

The counter 320 is configured to register at least a number of particles of radiation incident on the pixel 150 encompassing the electric contact 119B. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electric contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause at least one of the number registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include an integrator 309 electrically connected to the electric contact 119B, wherein the integrator is configured to collect charge carriers from the electric contact 119B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electric contact 119B accumulate on the capacitor over a period of time ("integration period"). After the integration period has expired, the capacitor voltage is sampled and then reset by a reset switch. The integrator 309 can include a capacitor directly connected to the electric contact 119B.

Figure 21:
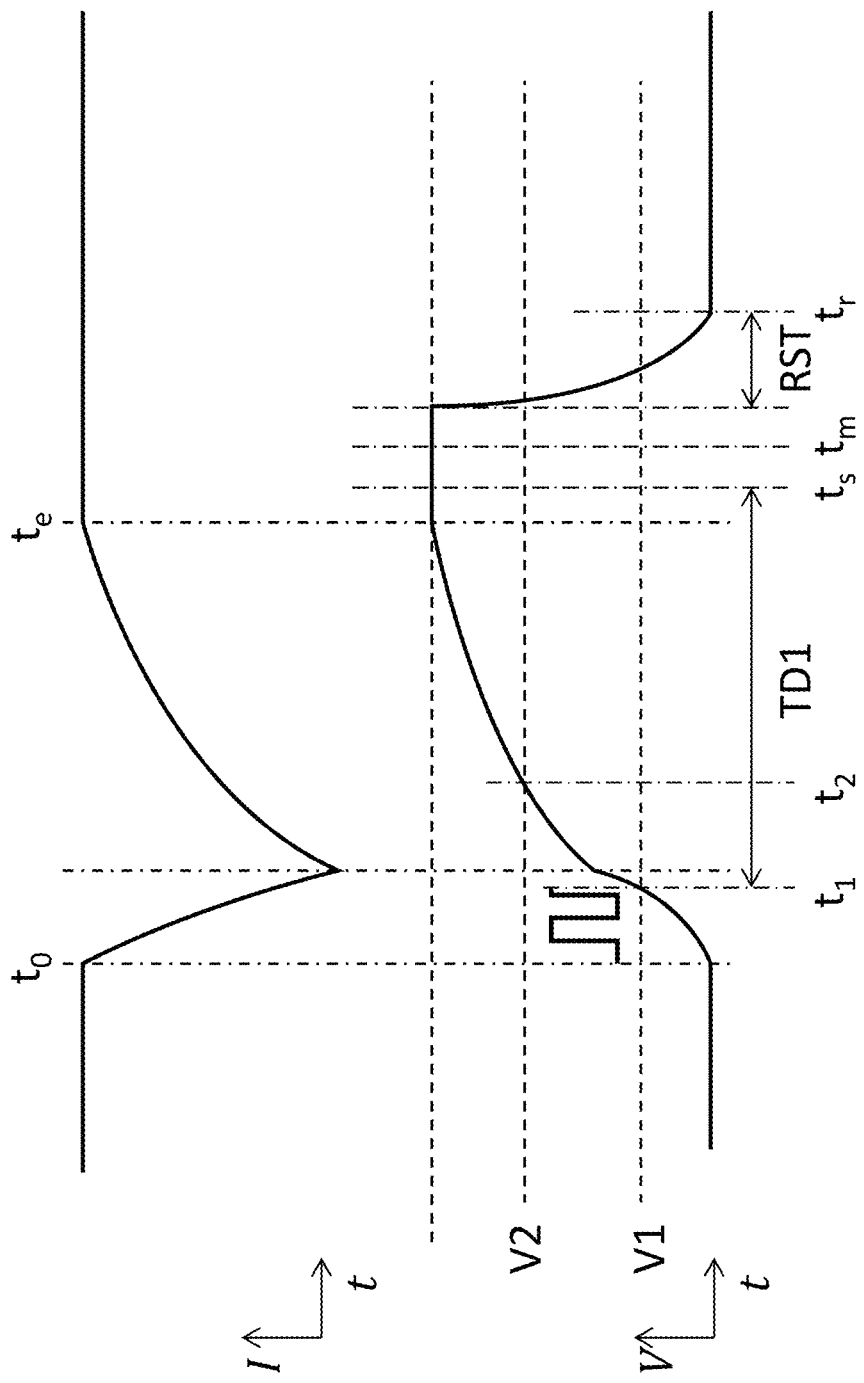
FIG. 21 schematically shows a temporal change of the electric current flowing through an electrode (upper curve) of a diode or an electric contact of a resistor of a radiation absorption layer exposed to radiation, the electric current caused by charge carriers generated by a radiation particle incident on the radiation absorption layer, and a corresponding temporal change of the voltage of the electrode (lower curve), according to an embodiment.

FIG. 21 schematically shows a temporal change of the electric current flowing through the electric contact 119B (upper curve) caused by charge carriers generated by a particle of radiation incident on the pixel 150 encompassing the electric contact 119B, and a corresponding temporal change of the voltage of the electric contact 119B (lower curve). The voltage may be an integral of the electric current with respect to time. At time $t_0$, the particle of radiation hits pixel 150, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the particle of radiation drift out of the radiation absorption layer 110. At time $t_s$, the time delay TD1 expires. At or after time $t_e$, the controller 310 causes the voltmeter 306 to digitize the voltage and determines which bin the energy of the particle of radiation falls in. The controller 310 then causes the number registered by the counter 320 corresponding to the bin to increase by one. In the example of FIG. 9, time $t_s$ is after time $t_e$; namely TD1 expires after all charge carriers generated by the particle of radiation drift out of the radiation absorption layer 110. If time $t_e$ cannot be easily measured, TD1 can be empirically chosen to allow sufficient time to collect essentially all charge carriers generated by a particle of radiation but not too long to risk have another incident particle of radiation. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the particle of radiation, which relates to the energy of the particle of radiation. The controller 310 may be configured to determine the energy of the particle of radiation, using the voltmeter 306.

After TD1 expires or digitization by the voltmeter 306, whichever later, the controller 310 connects the electric contact 119B to an electric ground for a reset period RST to allow charge carriers accumulated on the electric contact 119B to flow to the ground and reset the voltage. After RST, the electronic system 121 is ready to detect another incident particle of radiation. If the first voltage comparator 301 has been deactivated, the controller 310 can activate it at any time before RST expires. If the controller 310 has been deactivated, it may be activated before RST expires.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising:
   a radiation source;
   an image sensor;
   wherein the image sensor comprises a first radiation detector and a second radiation detector, respectively comprising a planar surface configured to receive radiation from the radiation source;
   wherein the planar surface of the first radiation detector and the planar surface of the second radiation detector are not parallel;
   wherein the first radiation detector and the second radiation detector are configured to move to a plurality of positions relative to the radiation source;
   wherein the image sensor is configured to capture, by using the first radiation detector and the second radiation detector and with the radiation, images of portions of a scene at the positions respectively, and configured to form an image of the scene by stitching the images of the portions;
   wherein the system is configured to rotate relative to the scene about a first axis;
   wherein the radiation source or the image sensor is on the first axis.

2. The system of claim 1, wherein a relative position of the first radiation detector with respect to the second radiation detector remains the same.

3. The system of claim 1, wherein the first radiation detector and the second radiation detector are configured to move relative to the radiation source by rotating about a second axis relative to the radiation source.

4. The system of claim 3, wherein the second axis is parallel to the planar surface of the first radiation detector and the planar surface of the second radiation detector.

5. The system of claim 3, wherein the first radiation detector and the second radiation detector are configured to move relative to the radiation source by rotating about a third axis relative to the radiation source; wherein the third axis is different from the second axis.

6. The system of claim 3, wherein the radiation source is on the second axis.

7. The system of claim 1, wherein the first radiation detector and the second radiation detector are configured to move relative to the radiation source by translating along a first direction relative to the radiation source.

8. The system of claim 7, wherein the first direction is parallel to the planar surface of the first radiation detector and the planar surface of the second radiation detector.

9. The system of claim 7, wherein the first direction is parallel to the planar surface of the first radiation detector but not parallel to the planar surface of the second radiation detector.

10. The system of claim 7, wherein the first radiation detector and the second radiation detector are configured to move relative to the radiation source by translating along a second direction relative to the radiation source; wherein the second direction is different from the first direction.

11. The system of claim 1, wherein the first radiation detector and the second radiation detector each comprise an array of pixels.

12. The system of claim 1, wherein the first radiation detector is rectangular in shape.

13. The system of claim 1, wherein the first radiation detector is hexagonal in shape.

14. The system of claim 1, wherein the system is configured to rotate relative to the scene about a fourth axis different from the first axis.

15. The system of claim 14, wherein the radiation source is on the fourth axis.

16. The system of claim 14, wherein the image sensor is on the fourth axis.

17. The system of claim 1, wherein the image sensor is configured to form images of the scene when the system is respectively at a plurality of rotational positions relative to the scene.

18. A method of using the system of claim 1, the method comprising:
   forming a first image of the scene with the image sensor while the system is at a first rotational position relative to the scene;
   rotating the system relative to the scene about the first axis to a second rotational position relative to the scene;

forming a second image of the scene with the image sensor while the system is at the second rotational position relative to the scene.

19. The method of claim 18, further comprising rotating the system relative to the scene about a fourth axis to a third rotational position relative to the scene; and forming a third image of the scene with the image sensor while the system is at the third rotational position relative to the scene; wherein the fourth axis is different from the first axis.

20. The method of claim 19, wherein the radiation source is on the fourth axis.

21. The method of claim 19, wherein the image sensor is on the fourth axis.

* * * * *